United States Patent
Moskal et al.

(10) Patent No.: US 9,101,612 B2
(45) Date of Patent: *Aug. 11, 2015

(54) SECONDARY STRUCTURE STABILIZED NMDA RECEPTOR MODULATORS AND USES THEREOF

(75) Inventors: Joseph Moskal, Evanston, IL (US); M. Amin Khan, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/578,189

(22) PCT Filed: Feb. 11, 2011

(86) PCT No.: PCT/US2011/024583
§ 371 (c)(1),
(2), (4) Date: Oct. 19, 2012

(87) PCT Pub. No.: WO2011/100585
PCT Pub. Date: Aug. 18, 2011

(65) Prior Publication Data
US 2013/0053325 A1    Feb. 28, 2013

Related U.S. Application Data

(60) Provisional application No. 61/303,472, filed on Feb. 11, 2010.

(51) Int. Cl.
| | | |
|---|---|---|
| *A61K 38/00* | (2006.01) | |
| *A61K 38/07* | (2006.01) | |
| *A61K 31/4025* | (2006.01) | |
| *C07D 487/10* | (2006.01) | |

(52) U.S. Cl.
CPC .......... *A61K 31/4025* (2013.01); *C07D 487/10* (2013.01)

(58) Field of Classification Search
None
See application file for complete search history.

(56) References Cited

U.S. PATENT DOCUMENTS

| | | | |
|---|---|---|---|
| 4,904,681 A | 2/1990 | Cordi et al. | |
| 4,959,493 A | 9/1990 | Ohfune et al. | |
| 5,061,721 A | 10/1991 | Cordi et al. | |
| 5,086,072 A | 2/1992 | Trullas et al. | |
| 5,166,136 A | 11/1992 | Ward et al. | |
| 5,350,769 A | 9/1994 | Kasai et al. | |
| 5,523,323 A | 6/1996 | Maccecchini | |
| 5,605,911 A | 2/1997 | Olney et al. | |
| 5,648,259 A | 7/1997 | Mallet et al. | |
| 5,741,778 A | 4/1998 | Martin et al. | |
| 5,763,393 A | 6/1998 | Moskal et al. | |
| 5,804,550 A | 9/1998 | Bourguignon | |
| 5,902,815 A | 5/1999 | Olney et al. | |
| 5,952,389 A | 9/1999 | Fogel | |
| 5,959,075 A | 9/1999 | Lok et al. | |
| 6,007,841 A | 12/1999 | Caruso | |
| 6,025,471 A | 2/2000 | Deghenghi | |
| 6,107,271 A | 8/2000 | Moskal et al. | |
| 6,147,230 A | 11/2000 | Shimamoto et al. | |
| 6,197,820 B1 | 3/2001 | Sontheimer et al. | |
| 6,521,414 B2 | 2/2003 | Melcher et al. | |
| 6,541,453 B2 | 4/2003 | Oldham et al. | |
| 6,635,270 B2 | 10/2003 | Hong et al. | |
| 6,667,317 B2 | 12/2003 | Chenard et al. | |
| 6,821,985 B2 | 11/2004 | Chenard et al. | |
| 7,273,889 B2 | 9/2007 | Mermelstein et al. | |
| 7,884,080 B2 | 2/2011 | Aslanian et al. | |
| 8,492,340 B2 | 7/2013 | Moskal | |
| 8,673,843 B2 | 3/2014 | Moskal et al. | |
| 2003/0022253 A1 | 1/2003 | Moskal | |
| 2003/0064921 A1 | 4/2003 | Millhauser et al. | |
| 2003/0175734 A1 | 9/2003 | Kroes et al. | |
| 2005/0037433 A1 | 2/2005 | Nakanishi et al. | |
| 2005/0118286 A1 | 6/2005 | Suffin et al. | |
| 2006/0241046 A1 | 10/2006 | Olivera et al. | |
| 2007/0087404 A1 | 4/2007 | Stahl et al. | |
| 2007/0208001 A1 | 9/2007 | Zhuo et al. | |
| 2011/0306586 A1 | 12/2011 | Khan et al. | |
| 2012/0178695 A1 | 7/2012 | Moskal | |
| 2012/0295852 A1 | 11/2012 | Moskal | |
| 2013/0005662 A1 | 1/2013 | Moskal | |
| 2013/0035292 A1 | 2/2013 | Moskal | |
| 2013/0053325 A1 | 2/2013 | Moskal et al. | |
| 2013/0136954 A1 | 5/2013 | Fujita et al. | |
| 2013/0288975 A1 | 10/2013 | Moskal | |
| 2013/0296248 A1 | 11/2013 | Moskal | |

(Continued)

FOREIGN PATENT DOCUMENTS

| | | |
|---|---|---|
| CN | 101066945 A | 11/2007 |
| CN | 101125817 A | 2/2008 |

(Continued)

OTHER PUBLICATIONS

Moskal et al., GLYX-13: A monoclonal antibody-derived peptide that acts as an N-methyl-D-aspartate receptor modulator, Neuropharmacology, 49 (2005) 1077-1087.*

Kulagowski et al., 3'-(Arylmethyl)- and 3'-(Aryloxy)-3-phenyl-4-hydroxyquinolin-2(1H)-ones: Orally Active Antagonists of the Glycine Site on the NMDA Receptor, J. Med. Chem., (1004), 37, 1402-1405.*

Jonson and Petersen, A critical view on conservative mutations, Prot. Eng. vol. 14, No. 6, pp. 397-402 (2001).*

(Continued)

*Primary Examiner* — Karlheinz R Skowronek
*Assistant Examiner* — Joseph Fischer
(74) *Attorney, Agent, or Firm* — Goodwin Procter LLP

(57) ABSTRACT

Disclosed are compounds having enhanced potency in the modulation of NMDA receptor activity. Such compounds are contemplated for use in the treatment of diseases and disorders such as learning, cognitive activities, and analgesia, particularly in alleviating and/or reducing neuropathic pain.

6 Claims, 16 Drawing Sheets

(56) References Cited

U.S. PATENT DOCUMENTS

| | | | |
|---|---|---|---|
| 2013/0310323 | A1 | 11/2013 | Moskal |
| 2013/0316954 | A1 | 11/2013 | Moskal |

FOREIGN PATENT DOCUMENTS

| | | | | |
|---|---|---|---|---|
| WO | WO-97/43306 | A1 | 11/1997 | |
| WO | WO-99/02733 | A1 | 1/1999 | |
| WO | WO-99/24584 | A1 | 5/1999 | |
| WO | WO-99/51985 | A1 | 10/1999 | |
| WO | WO-00/28090 | A2 | 5/2000 | |
| WO | WO-01/36685 | A2 | 5/2001 | |
| WO | WO-01/96606 | A2 | 12/2001 | |
| WO | WO-01/98367 | A2 | 12/2001 | |
| WO | WO-02/47535 | A2 | 6/2002 | |
| WO | WO-02/072609 | A2 | 9/2002 | |
| WO | WO-03/010540 | A1 | 2/2003 | |
| WO | WO-2005/020973 | A2 | 3/2005 | |
| WO | WO 2007027559 | A1 * | 3/2007 | ............. A61K 38/00 |
| WO | WO-2009/039390 | A2 | 3/2009 | |
| WO | WO-2010/015545 | A1 | 2/2010 | |
| WO | WO-2010/033757 | A1 | 3/2010 | |
| WO | WO-2010/065709 | A2 | 6/2010 | |
| WO | WO-2011/003064 | A1 | 1/2011 | |
| WO | WO-2011/044089 | A2 | 4/2011 | |
| WO | WO-2011/100585 | A1 | 8/2011 | |
| WO | WO-2012/149389 | A2 | 11/2012 | |

OTHER PUBLICATIONS

Abramets et al. (2008) "Neurophysiological and neurochemical aspects of the effects of antidepressants and mood stabilizers," *Neurophysiology, Kluwer Academic Publishers-Plenum Publishers*. 40(1):64-78.
Burgdorf et al. (2012) "GLYX-13, an NMDA Receptor Glycine-Site Functional Partial Agonist, Induces Antidepressant-Like Effects Without Ketamine-Like Side Effects" *Nature*. Accepted Article Preview, doi: 10.1038/npp.2012.246 (46 pages).
Burgdorf et al. (2010) "The Antidepressant and Anxiolytic Properties of GLYX-13: A Novel NMDA Receptor Glycine Site Functional Partial Agonist," *Abstracts of the Annual Meeting of the Society for Neuroscience, Society for Neuroscience*. Jan. 1, 2010 (2 pages).
Extended European Search Report for EP10822514.5 dated Feb. 13, 2013.
Krystal et al. (1999) "NMDA Agonists and Antagonists as Probes of Glutamatergic Dysfunction and Pharmacotherapies in Neuropsychiatric," *Harvard Review of Psychiatry*. 7(3):125-143.
Pittenger et al. (2007) "The NMDA Receptor as a Therapeutic Target in Major Depressive Disorder," *CNS& Neurological Disorders Drugs Targets*. 6(2):101-115.
Moskal, J.R. and Schaffner, A.E. "Monoclonal antibodies to the dentate gyrus: Immunocytochemical characterization and flow cytometric analysis of hippocampal neurons bearing unique cell surface antigen" *J. Neurosci*. (1986) 6(7): 2045-2053.
M.J. Schell, "The N-methyl D-aspartate receptor glycine site and D-serine metabolism: an evolutionary perpective," *Phil. Trans. R. Soc. Lond. B*. (2004) 359, 943-964.
Sugimoto et al., "Evidence for the involvement of $GABA_A$ receptor blockade in convulsions induced by cephalosporins." *Neuropharmacology*. (2003) 45:304-314.
European Search Report for EP11761468.5 dated Jun. 12, 2013, 6 pages.
Abbott et al. (1995) "The Formalin Test: Scoring Properties of the First and Second Phases of the Pain Response in Rats," *Pain*, 60(1):91-102.
Alonso et al. (2001) "Spiro-Beta-Lactams as Beta-Turn Mimetics. Design, Synthesis, and NMR Conformational Analysis," *J. Org. Chem*., 66(19):6333-6338.
Bennett et al. (1988) "A Peripheral Mononeuropathy in Rat That Produces Disorders of Pain Sensation Like Those Seen in Man," *Pain*, 33(1): 87-107.

Bittermann et al. (2006) "Chirospecific Synthesis of Spirocyclic Beta-Lactams and Their Characterization as Potent Type II beta-Turn Inducing Peptide Mimetics," *J. Org. Chem*., 71(1):97-102.
Bittermann et al. (2006) "A Highly Practical RCM Approach Towards a Molecular Building Kit of Spirocyclic Reverse Turn Mimics," *Chemistry*, 12(24):6315-6322.
Burch et al. (2010) "GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder," *NCDEU*, Jun. 16, 2010, Naurex, Inc. (1 page).
Burgdorf et al. (2008) "Uncovering the Molecular Basis of Positive Affect Using Rough-and-Tumble Play in Rats: A Role for the NMDA Receptor and Implications for Depression," (2 pages) (Poster #393. 1/UU11) *Neuroscience 2008*, Nov. 17, 2008.
Burgdorf et al. (2010) "The Antidepressant and Anxiolytic Properties of GLYX-13: A Novel NMDA Receptor Glycine Site Functional Partial Agonist," (Poster #198) *ACNP 2010*, Dec. 6, 2010 (1 page).
Burgdorf et al. (2011) "The N-Methyl-D-Aspartate Receptor Modulator GLYX-13 Enhances Learning and Memory, in Young Adult and Learning Impaired Aging Rats," *Neurobiol. Aging*, 32(4):698-706.
Careri et al. (2003) "Pentacopper(II) 12-Metallacrown-4 Complexes with Alpha- and Beta-Aminohydroxamic Acids in Aqueous Solution: A Reinvestigation," *J. Inorg. Biochem*., 93(3-4):174-180.
Coates et al. (2005) "Product Class 9: Beta-Lactams," *Science of Synthesis*, 21:609-646.
Cremonesi, et al. (2010) "Enantiomerically Pure Polyheterocyclic Spiro-beta-Lactams from trans-4-Hydroxy-L-proline," *J. Org. Chem*., 75(6):2010-2017.
Croce et al. (1999) "Reaction of Mesoionic Compounds Deriving from Cyclic N-Acyl-alpha-amino Acids with N-(Phenylmethylene)benzenesulfonamide," *Tetrahedron*, 55(1):201-210.
Croce et al. (1999) "Stereoselective Synthesis of N-Phenylsulfonyl Substituted Spiro-beta-Lactams," *Tetrahedron: Asymmetry*, 10(6):1193-1199.
Database Registry [Online] Chemical Abstracts Service, Columbus, Ohio US; Sep. 28, 2008, XP002668993, Database Accession No. 1053605-89-2.
Database Registry [Online] Chemical Abstracts Service, Columbus, Ohio, US; Jul. 1, 2008 XP002668992, Database Accession No. 1031928-30-9.
del Pozo et al. (2004) "Diastereo- and Enantioselective Synthesis of Novel beta-Lactam-Containing 1,4-Benzodiazepines Through a Ketene-Imine Cycloaddition Reaction" *Eur. J. Org. Chem*., (3):535-545.
European Search Report for Application No. EP 09 81 5233 completed on Feb. 8, 2012 and dated May 22, 2012.
Forni (1998) "Two Diastereoisomers of 2-(Benzenesulfonyl)-5-benzoyl-1-oxo-3-phenyl-2,5-diazaspiro[3.4]octan-7-yl acetate," *Acta Crystallographica Section C: Crystal Structure Communications*, C54(9):1320-1322.
Foster et al. (1987) "Neurobiology: Taking Apart NMDA Receptors," *Nature*, 329:395-396.
Golik (1972) "Synthesis of Malonimide Derivatives as Potential Penicillin Analogs," *J. Heterocycl. Chem*., 9(1):21-4.
Grigg et al. (1995) "X=Y–ZH Systems as Potential 1,3-Dipoles. Part 46. Cascade 1,3-Dipolar Cycloaddition Reactions of Cephalosporin Imines," *Tetrahedron*, 51(48):13347-56.
Haring et al. (1987) "Binding Studies and Photoaffinity Labeling Identify Two Classes of Phencyclidine Receptors in Rat Brain," *Biochemistry*, 26:5854-5861.
Haring et al. (1986) "Identification of Polypeptides of the Phencyclidine Receptor of Rat Hippocampus by Photoaffinity Labeling with [H3]Azidophencyclidine," *Biochemistry*, 25:612-620.
Haring et al. (1987) "Multiple Mode of Binding of Phencyclidines: High Affinity Association Between Phencyclidine Receptors in Rat Brain and a Monovalent Ion-Sensitive Polypeptide," *Biochem. Biophys. Res. Comm*., 142(2):501-510.
Haring et al. (1991) "Glycine-Like Modulation of N-Methyl-D-Aspartate Receptors by a Monoclonal Antibody that Enhances Long-Term Potentiation," *J. Neurochem*., 57(1):323-332.

(56) References Cited

OTHER PUBLICATIONS

Holderback et al. *Biol Psych.*, Published online Dec. 2006, 62:92-100.
Johnson et al. (2003) "The Preparation of a Double Metallahelicate Containing 28 Copper Atoms," *Angew. Chem. Int. Ed. Engl.*, 42(5):546-549.
Johnson, et al. (1990) "Neuropharmacolgy of Phencyclidine: Basic Mechanisms and Therapeutic Potential," *Annu. Rev. Pharmacol. Toxicol.*, 30:707-750.
Khasanov et al. (2004) "Novel Asymmetric Approach to Proline-Derived Spiro-beta-lactams," *J. Org. Chem.*, 69(17):5766-5769.
Kloog et al. (1988) "Kinetic Characterization of the Phencyclidine-N-Methyl-d-aspartate Receptor Interaction: Evidence for a Steric Blockade of the Channel," *Biochemistry*, 27(3):843-848.
Kloog et al. (1988) "Mode of Binding of [3H]dibenzocycloalkenimine (MK-801) to the N-methyl-D-aspartate (NMDA) Receptor and its Therapeutic Implication," *FEBS Lett.*, 230(1-2):167-70.
Koller et al. (2010) "Novel N-Methyl-D-aspartate Receptor Antagonists: A Review of Compounds Patented Since 2006," *Expert Opin. Ther. Patents*, 20(12):1683-1702.
Kroes et al. (2006) "Development of a Novel Glycobiologic Therapy for Glioblastoma," *Neuro-oncol.* 8(4):397-398, Oct. 2006, Abstract CB-14, 2 pages.
Kroes et al. (2006) "Development of a Novel Glycobiology-Based Therapeutic for Glioblastoma," *J. Neurochem.*, 99(Suppl. 1):17, Nov. 10, 2006, Abstract 50, 1 page.
Leander et al. (2010) "Lack of Ketamine-Like Discriminative Effects of GLYX-13: A Novel NMDA Receptor Glycine Site Functional Partial Agonist with Antidepressant-Like Preclinical Effects," *ACNP*, Dec. 2010, 218 (1 page).
Li et al. (2007) "N-Heterocyclic Carbene Catalyzed Ring Expansion of 4-Formyl-beta-lactams: Synthesis of Succinimide Derivatives," *Org. Lett.*, 9(18):3519-3521.
Lynch et al. (2006) "Synaptic Plasticity in Early Aging," *Aging Research Reviews*, 5:255-280.
Macias et al. (2004) "Diastereoselective [2+2]-Cycloaddition Reactions of Unsymmetrical Cyclic Ketenes with Imines: Synthesis of Modified Prolines and Theoretical Study of the Reaction Mechanism," *J. Org. Chem.*, 69(21):7004-7012.
Macias et al. (2004) "Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands," *Tetrahedron Lett.*, 45(24):4657-4660.
Macias et al. (2006) "Synthesis of Enantiopure Pyrrolidine-Derived Peptidomimetics and Oligo-beta-peptides via Nucleophilic Ring-Opening of beta-Lactams," *J. Org. Chem.*, 71(20):7721-7730.
Mayer et al. (1990) "Excitatory Amino Acid Receptors, Second Messengers and Regulation of Intracellular Ca2+ in Mammalian Neurons," *Trends in Pharmacol. Sci.*, 11:254-260.
Mishra et al. (2002) "Three-Dimensional Quantitative Structure-Activity Relationship and Comparative Molecular Field Analysis of Dipeptide Hydroxamic Acid *Helicobacter pylori* Urease Inhibitors," *Antimicrob. Agents and Chemother.*, 46(8):2613-2618.
Monahan et al. (1989) "D-Cycloserine, a Positive Modulator of the N-Methyl-d-Aspartate Receptor, Enhances Performance of Learning in Rats," *Pharm. Biochem. Behav.*, 34:649-653.
Moskal et al. (2009) "The Antidepressant and Anxiolytic Properties of GLYX-13: A Novel NMDA Receptor Glycine Site Functional Partial Agonist," (Poster #059) ACNP 2009, Dec. 7, 2009 (1 page).
Moskal et al. (1996) "Monoclonal Antibodies to the Dentate Gyrus: Immunocytochemical Characterization and Flow Cytometric Analysis of Hippocampal Neurons Bearing a Unique Cell-Surface Antigen," *J. Neurosci*, 6(7):2045-2053.
Moskal et al. (2001) "The Use of Antibody Engineering to Create Novel Drugs that Target N-Methyl-D-aspartate Receptors," *Current Drug Targets*, 2:331-345.
Moskal et al. (2005) "GLYX-13: A Monoclonal Antibody-Derived Peptide that Acts as an N-Methyl-D-aspartate Receptor Modulator," *Neuropharmacology*, 49:1077-1087.
Moskal et al. (2010) "A Novel Approach to Unlocking the Therapeutic Potential of the NMDA Receptor," *Vital Signs e-magazine*, Sep. 2010 (2 pages).
Moskal, et al. (2009) "The anti-depressant and anxiolytic properties of GLYX-13: a Glycine-site Functional Partial Agonist (GFPA), a novel mechanism for modulating NMDA receptors," *ACNP Annual Meeting*, (Dec. 2009) (2 pages) (Abstract).
Narahashi et al. (2004) "Mechanisms of Action of Cognitive Enhancers on Neuroreceptors," *Biol. Pharm. Bull.*, 27(11):1701-1706.
NCBI Submission NM_000149, 1990, Retrieved from the internet; <URL:http://www.ncbi.nlm.nih.gov/nuccore/148277008>, 5 pages.
NCBI Submission NM_001276, 1989, Retrieved from the internet; <URL:http://www.ncbi.nlm.nih.gov/nuccore/144226250>, 5 pages.
NCBI Submission NM_030965, 1989, Retrieved from the internet; <URL:http://www.ncbi.nlm.nih.gov/nuccore/13569957>, 3 pages.
NCBI Submission NM_173216, 1989, Retrieved from the internet; <URL:http://www.ncbi.nlm.nih.gov/nuccore/27765090>, 5 pages.
Overman et al. (1985) "A Convenient Synthesis of 4-Unsubstituted beta-Lactams," *J. Am. Chem. Soc.*, 107(6):1698-701.
Parac-Vogt et al. (2005) "Pentacopper(II) Complexes of alpha-Aminohydroxamic Acids: Uranyl-Induced Conversion of a 12-Metallacrown-4 to a 15-Metallacrown-5," *J. Inorg. Biochem.*, 99(2):497-504.
Raghavan et al. (2009) "Allosteric Modulation of the Dopamine D2 Receptor by Pro-Leu-Gly-NH2 Peptidomimetics Constrained in Either a Polyproline II Helix or a Type II beta-Turn Conformation," *J. Med. Chem.*, 52(7):2043-2051.(7):2043-2051.
Ransom et al. (1988) "Cooperative Modulation of [3H]MK-801 Binding to the N-Methyl- d-Aspartate Receptor-Ion Channel Complex by I-Glumate, Glycine, and Polyamines," *J. Neurochem.* 51:830-836.
Rasmusson et al. (1973) "6-Substituted Penicillin Derivatives," VI. *Tetrahedron Lett.*, (2):145-8.
Siemion et al. (1988) "Conformational Preferences of the Sequential Fragments of the Hinge Region of the Human IgA1 Immunoglobulin Molecule," *Biophys. Chem.*, 31:35-44.
Stanton et al. (1987) "Inhibition of the Production and Maintenance of Long-Term Potentiation in Rat Hippocampal Slices by a Monoclonal Antibody," *Proc. Natl. Acad. Sci. USA*, 84:1684-1688.
Stanton et al. (2009) "Neuroprotection by a Novel NMDAR Functional Glycine Site Partial Agonist, GLYX-13," *Neuropharmacology and Neurotoxicology NeuroReport*, 00(00):1-5.
Tanwar et al. (2002) "Gene Expression Microarray Analysis Reveals YLK-40 to be a Potential Serum Marker for Malignant Character in Human Glioma," *Cancer Res.*, 62:4364-4368.
Thompson et al. (1992) "Hippocampus-Dependent Learning Facilitated by a Monoclonal Antibody or D-Cycloserine," *Nature*, 359:638-641.
Turturro et al. (1999) "Growth Curves and Survival Characteristics of the Animals Used in the Biomarkers of Aging Program," *Journal of Gerontology: Biological Sciences*, 54A(11):B492-B501.
Wood (2005) "The NMDA Receptor Complex: A Long and Winding Road to Therapeutics," *IDrugs*, 8(3):229-235.
Wood et al. (2008) "Antinociceptive Action of GLYX-13: An N-Methyl-D-aspartate Receptor Glycine Site Partial Agonist," *NeuroReport* 19(10):1061-1063.
Wood et al. (1989) "Tetrapeptide Inhibitors of the IgA1 Proteinases from Type I *Neisseria gonorrhoeae*," *J. Med. Chem.* 32:2407-2411.
Zhang et al. (2008) "A NMDA Receptor Glycine Site Partial Agonist, GLYX-13, Simultaneously Enhances LTP and Reduces LTD at Schaffer Collateral-CA1 Synapses in Hippocampus," *Neuropharmacology*, 55:1238-1250.
Kulagowski et al. "3'-(Arylmethyl)- and 3'-(aryloxy)-3-phenyl-4-hydroxyquinolin-2(1H)-ones: orally active antagonists of the glycine site on the NMDA receptor" *J Med Chem.* May 13, 1994;37(10):1402-5.
Office Action for U.S. Appl. No. 13/578,189, mailed Oct. 31, 2013.
British Medical Journal. 1980, pp. 1037-1038.
Chilman-Biair et al. Drugs of the Future, 2003, Abstract.

(56) References Cited

OTHER PUBLICATIONS

Lake et al. "Schizoaffective disorder merges schizophrenia and bipolar disorders as one disease—there is no schizoaffective disorder." Curr. Opin. Psych., 2007, vol. 20, Issue 4, pgs. Abstract.
NIMH—Bipolar Disorder. Published online 2013, pp. 1-9.
NIMH Mental Health Institute. Sciences News, 2013, pp. 1-5.
Stahl, "Novel therapeutics for schizophrenia: targeting glycine modulation of NMDA glutamate receptors" CNS Spectr., 2007, vol. 12, Issue 6, pp. 423-427.
International Search Report and Written Opinion for International Application No. PCT/US2011/024583, mailed Jul. 26, 2011, 7 pages.

\* cited by examiner

Sequence from 1PDB7: Fragment, Ligand Binding Core (SEQ ID NO. 1):

```
G                                                                    1
MSTRLKI                                                              8
VTIHQEPFVY VKPTMSDGTC KEEFTVNGDP VKKVICTGPN DTSPGSPRHT               58
VPQCCYGFCI DLLIKLARTM NFTYEVHLVA DGKFGTQERV NNSNKKEWNG              108
MMGELLSGQA DMIVAPLTIN NERAQYIEFS KPFKYQGLTI LVKK                    152

GT                                                                  154
RITGINDP                                                            162
RLRNPSDKFI YATVKQSSVD IYFRRQVELS TMYRHMEKHN YESAAEAIQA              212
VRDNKLHAFI WDSAVLEFEA SQKCDLVTTG ELFFRSGFGI GMRKDSPWKQ              262
NVSLSILKSH ENGFMEDLDK TWVRYQECDS                                    292
```

GLYX-13:
1) Proline 124
2) Threonine 126
3) Glutamine 178
4) Serine 180

DCKA
1) Threonine 126
2) Arginine 131

DCS
1) Proline 124
2) Threonine 126
3) Arginine 131
4) Asparte 224

D-serine/glycine
1) Threonine 126
2) Arginine 131
3) Serine 180
4) Asparte 224

Fig. 9

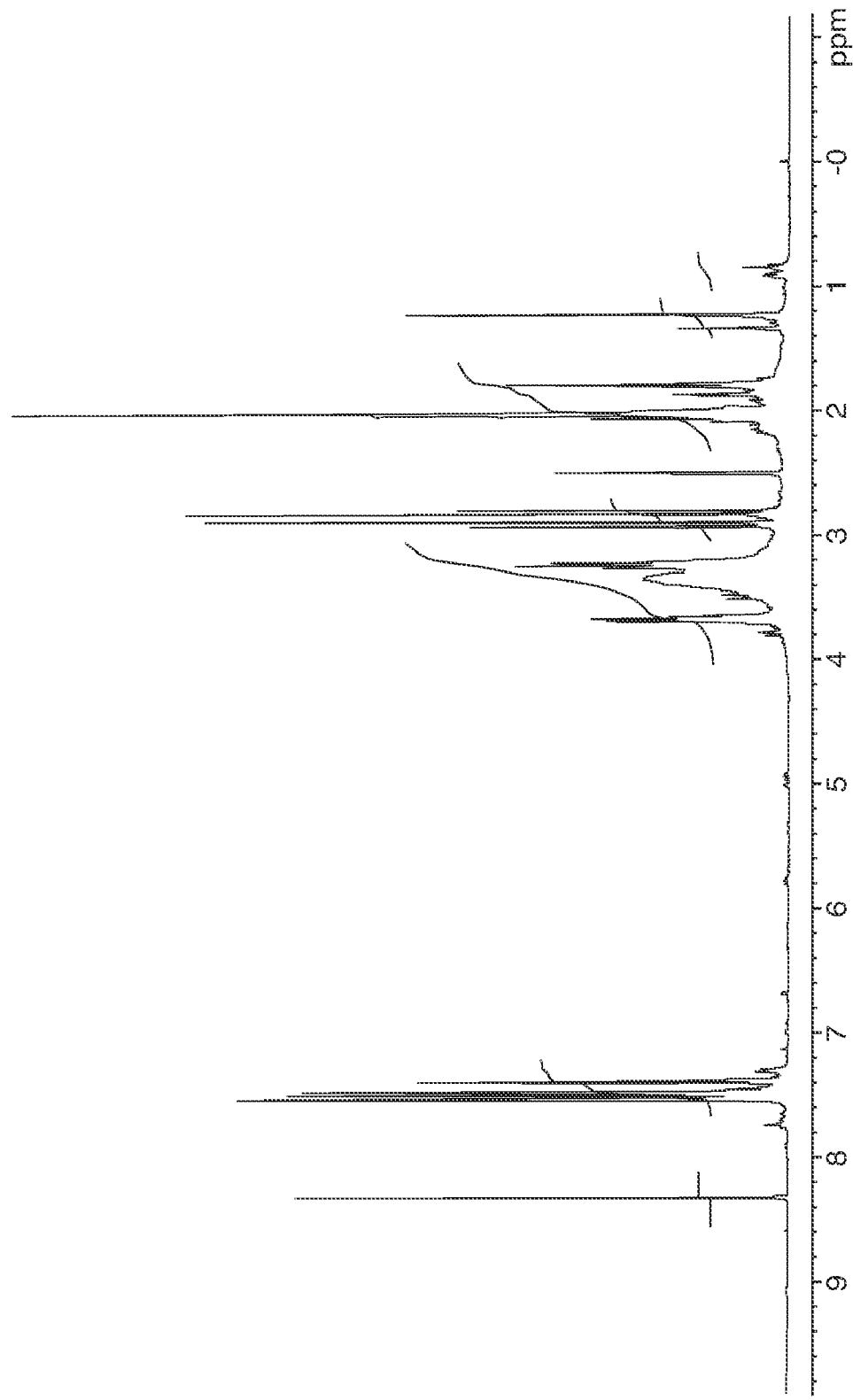

SECONDARY STRUCTURE STABILIZED NMDA RECEPTOR MODULATORS AND USES THEREOF

CROSS REFERENCE TO RELATED APPLICATIONS

This application is a national stage filing under 35 U.S.C. 371 of PCT/US2011/24583, filed Feb. 11, 2011, which claims priority to U.S. Ser. No. 61/303,472, filed Feb. 11, 2010, all of which are incorporated by reference in their entirety.

SEQUENCE LISTING

The instant application contains a Sequence Listing which has been submitted electronically in ASCII format and is hereby incorporated by reference in its entirety. Said ASCII copy, created on Sep. 10, 2014, is named NAU-004_SL.txt and is 3,895 bytes in size.

BACKGROUND

An N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding to, or modulating the glycine binding site of NMDA receptors, e.g the NMDA receptor NR1 ligand binding core, with e.g. with significant specificity and/or potency, especially in-vivo, to provide pharmaceutical benefits. In addition, a need continues to exist in the medical arts for an orally deliverable forms of such compounds.

SUMMARY

Provided herein, at least in part, are compounds that are NMDA modulators, for example, partial agonists of NMDA. For example, provided herein are compounds that can mimic a beta-turn structure that is capable of selectively interacting with the glycine binding region of NMDA receptor NR1, e.g. SEQ ID. NO. 1. Disclosed peptide mimetics, for example, have a beta-turn motif when binding to SEQ ID NO. 1. In some embodiments, disclosed peptide mimetics substantially maintain a beta-turn motif in vivo or in an aqueous solution.

In some embodiments, a peptide mimetic capable of binding to, or associating with, the NMDA ligand binding core of SEQ ID NO. 1 is provided, wherein said peptide mimetic has at least two alpha carbons about 6 to about 14 Å apart, e.g., about 6 to about 8 Å apart. For example, disclosed mimetics may include a cyclic amide core, e.g. a spiro-beta-lactam.

In another embodiment, a disclosed peptide mimetic may be a peptide having two or three amino acids replaced with a moiety having a carboxyl group and an amino group. In an embodiment, a disclosed peptide mimetic of any one of claims 1-6, where said peptide mimetic is capable of forming a hydrogen bond at least one, two, three or four of the following amino acids of SEQ ID NO.1: PRO124, THR126, GLU178 and SER180, or may be capable of forming a hydrogen bond with all four amino acids.

For example, provided herein is a peptide mimetic capable of binding to the NMDA ligand binding core of SEQ ID NO. 1, wherein said peptide mimetic has two alpha carbons about 6 to about 14 Å apart, (e.g., about 6 to about 10 Å apart) and a beta-turn motif comprising a bicyclic amide core (e.g., a spiro-beta-lactam) such that, when the peptide mimetic binds to said SEQ ID NO. 1, the bicyclic amide core substantially retains configuration. Such peptide mimetic may include a core represented by:

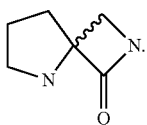

Exemplary peptide mimetics may substantially maintains the beta-turn motif in vivo or in an aqueous solution, and may be capable of forming a hydrogen bond with the following amino acids of SEQ ID NO.1: PRO124, THR126, GLU178 and SER180. In some embodiments, the beta-turn core may be conjugated to one or two amino acids.

Methods of treating or preventing a NMDA receptor mediated disorders in a patient are also provided, comprising administering to a patient in need thereof an acceptable NMDA ligand binding core receptor agonistic or antagonistic amount of a glycine mimicking beta-turn peptidomimetic cyclic compound having a cyclic amide moiety, for example, a beta-lactam moiety.

Also provided herein is a method of modulating the activity of SEQ ID NO. 1, wherein the modulation arises from a favorable conformation adopted by a compound, and wherein said modulation arises from a hydrogen bonding interaction between the compound and one, two, three or four of the following amino acids of SEQ ID NO.1: PRO124, THR126, GLU178 and SER180.

In another embodiment, a method of identifying a compound capable of binding to SEQ ID NO. 1 is provided, comprising: a) providing a molecular model comprising one or more target regions of SEQ ID NO. 1 derived from at least a portion of: SEQ ID NO. 1, atomic coordinates by molecular modeling of SEQ ID NO. 1, or atomic coordinates deposited in the Protein Data Bank under accession number 1PBQ; b) using the molecular model to identify a compound that can bind to the one or more target regions in the molecular model; and c) producing the compound. In some embodiments, such a method may further comprise the additional step of determining whether the compound modulates SEQ ID NO. 1.

Also provided herein are pharmaceutically acceptable compositions comprising a disclosed compound, and a pharmaceutically acceptable excipient. For example, such compositions may be suitable for oral administration to a patient.

A method for treating a cognitive disorder, such as a disorder associated with memory loss or impaired learning comprising administering to an patient in need thereof an effective amount of a disclosed compound. For example, provided herein are methods of treating or ameliorating memory loss or impaired learning in a patient in need thereof.

In an embodiment, methods for treating neuropathic pain in a patient in need thereof comprising administering an effective amount of a disclosed compound is provided.

Also disclosed herein are methods for treating depression, obsessive-compulsive disorder, or schizophrenia in a patient in need thereof comprising administering an effective amount of a disclosed compound. In another embodiment, methods for treating post traumatic stress disorder, an alcohol dependency disorder, or an addiction to an addictive drug in a patient in need thereof comprising administering an effective amount of a disclosed compounds are provided.

DESCRIPTION OF FIGURES

FIG. 9 depicts the sequence of the NMDA receptor NR1 and various compounds that associate via hydrogen bonding to specific amino acids.

FIG. 13 depicts a $^1$H NMR spectra of a compound disclosed herein.

DETAILED DESCRIPTION

Figure 1A:
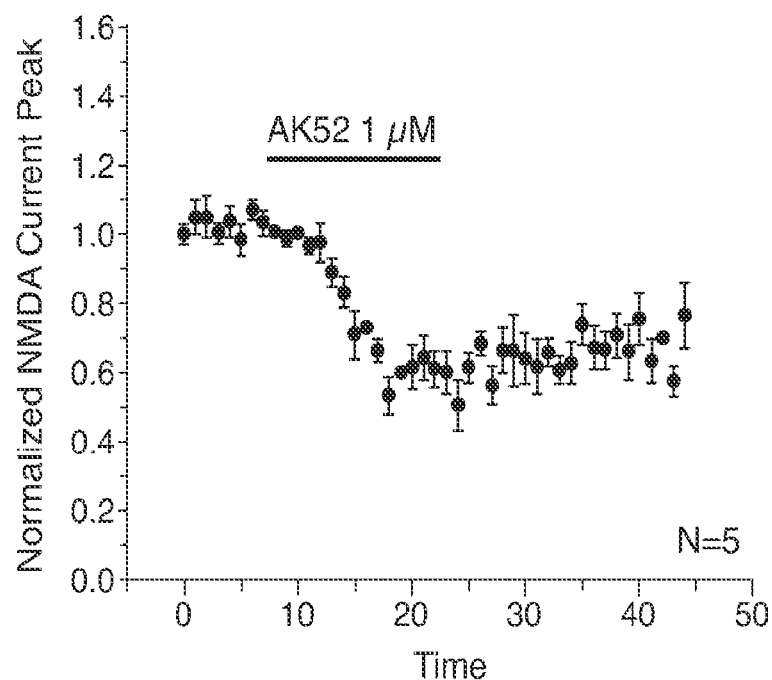
FIGS. 1A-1D indicate that a disclosed compound (AK52) biphasically alters postsynaptic NMDA receptor-mediated excitatory postsynaptic currents (e.p.s.c.s) at Shaffer collateral-CA1 synapses, and selectively enhances induction of LTP. 1A: Time course of the marked reduction by AK52 (1 µM; solid bar) of the NMDA component of Schaffer collateral-evoked e.p.s.c.s in CA1 pyramidal neurons. (Each point is the mean±SEM of e.p.s.c. peNRXe amplitude of 5 cells.) 1B: Time course of the enhancement of a ten-fold lower concentration of AK52 (100 NM; grey bar) of the NMDA component of Schaffer collateral-evoked e.p.s.c.s. in CA1 pyramidal neurons. (Each point is the mean±SEM of e.p.s.c. peNRX amplitude of 5 cells). 1C: Time course of LTD induced by a low frequency stimulus train (2 Hz/10 min; Starting at arrow) at Schaffer collateral-CA1 synapses in slices pre-treated with 1 µM (filled circles; n=10) and 100 nM (filled diamonds; n=6) NRX-10,052, compared to control, untreated slices (open circles; n-8). (Each point is the mean±SEM of normalized extracellular field EPSP slope of n slices.) 1D: Time course of experiments comparing LTP induced by a high frequency stimulus train (3×100 Hz/500 ms; arrow) at Schaffer collateral-CA1 synapses in slices pre-treated with 1 µM (filled circles; n=10 or 100 nM (filled diamonds; n=8) NRX-10,052, compared to control, untreated slices (open circles; n=15). (Each point is the mean±SEM of normalized field e.p.s.p. lsope of n slices).
Figure 1B:
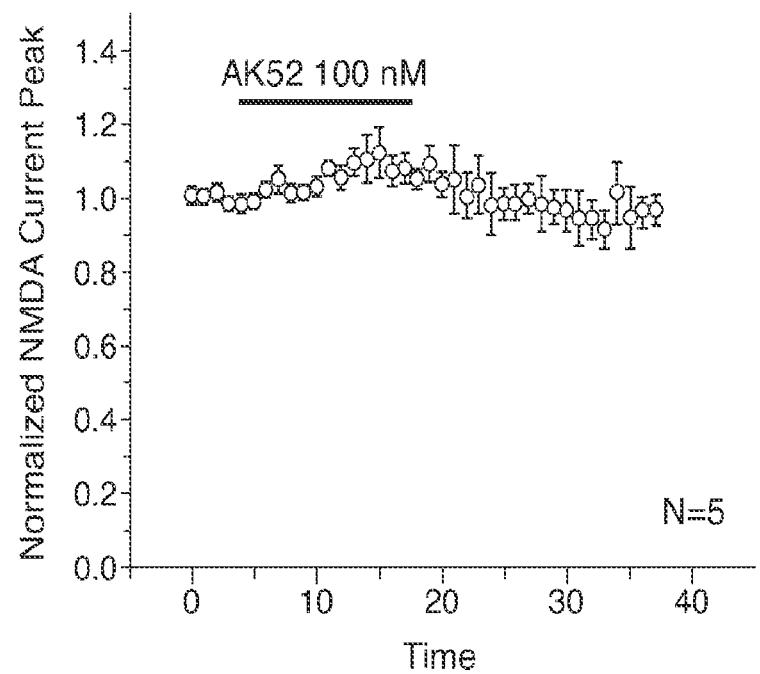
Figure 1C:
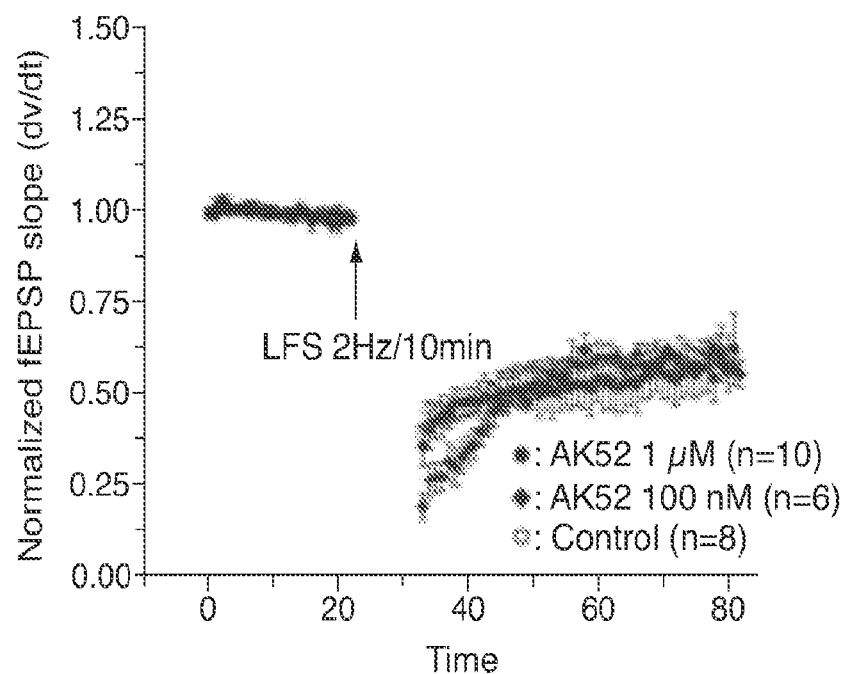
Figure 1D:
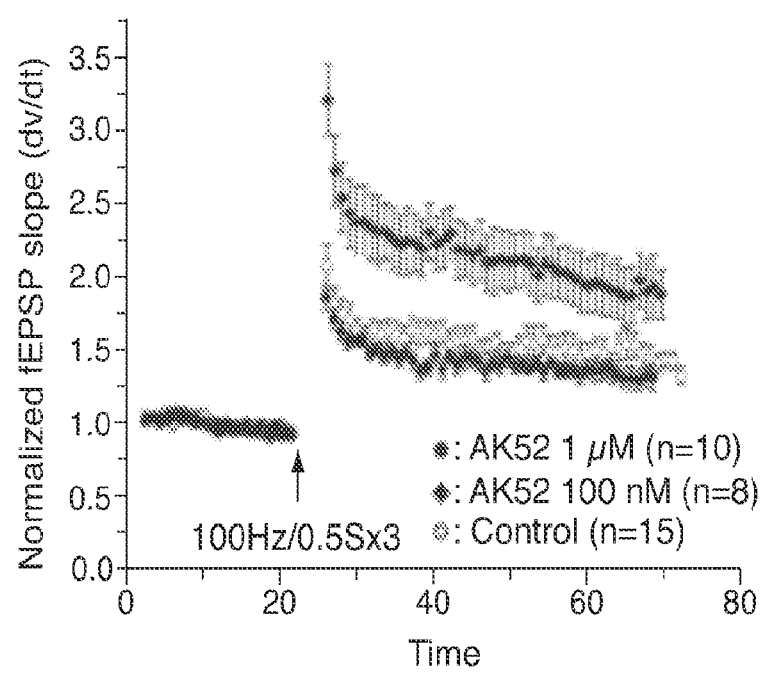
Figure 2A:
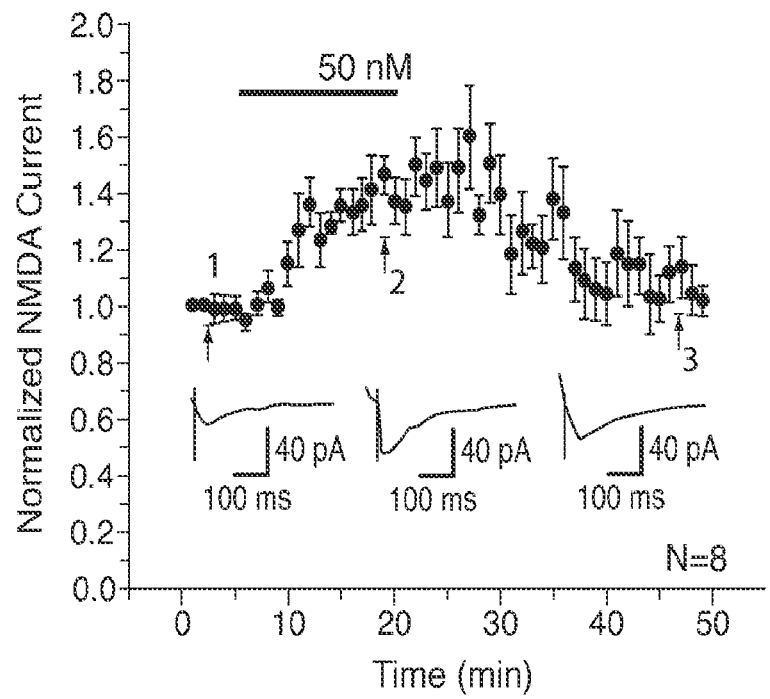
FIGS. 2A-2E indicate a low concentration of a disclosed compound B markedly enhances pharmacologically-isolated postsynaptic NMDA receptor-mediated excitatory postsynaptic currents (e.p.s.c.s) at Shaffer collateral-CA1 synapses and potentiates LTP, while a 20-fold higher concentration reduces NMDA e.p.s.c.s. 2A: Time course of the marked enhancement by Compound B (50 nM; solid bar) of single shock Schaffer collateral-evoked pharmacologically-isolated NMDA e.p.s.c.s. recorded in CA1 pyramidal neurons. 2B: Time course of the enhancement by compound B (50 nM; solid bar) of burst-evoked (4 pulses/100 Hz) NMDA e.p.s.c.s. 2C: Time course of the marked reduction by compound B (1 µM; solid bar) of single shock Schaffer collateral-evoked NMDA e.p.s.c.s. recorded in CA1 pyramidal neurons. 2D: Time course of the reduction by compound B (1 µM; solid bar) of burst-evoked (4 pulses 100 Hz) Schaffer collateral-evoked NMDA e.p.s.c.s recorded in CA1 pyramidal neurons. 2E: Enhancement of high frequency (100 Hz/500 ms×3; solid arrow) Schaffer collateral stimulus-evoked LTP at synapses on CA1 pyramidal neurons by 50 nM Compound B (filled circles) compared to control, untreated slices (open circles). (Each point is the mean±SEM of e.p.s.c. peNRX amplitude of n cells.).
Figure 2B:
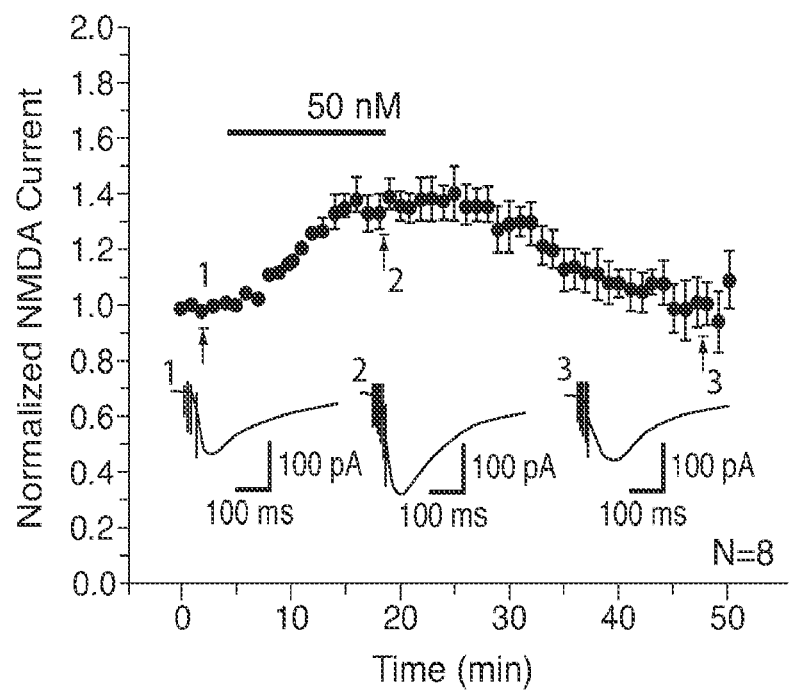
Figure 2C:
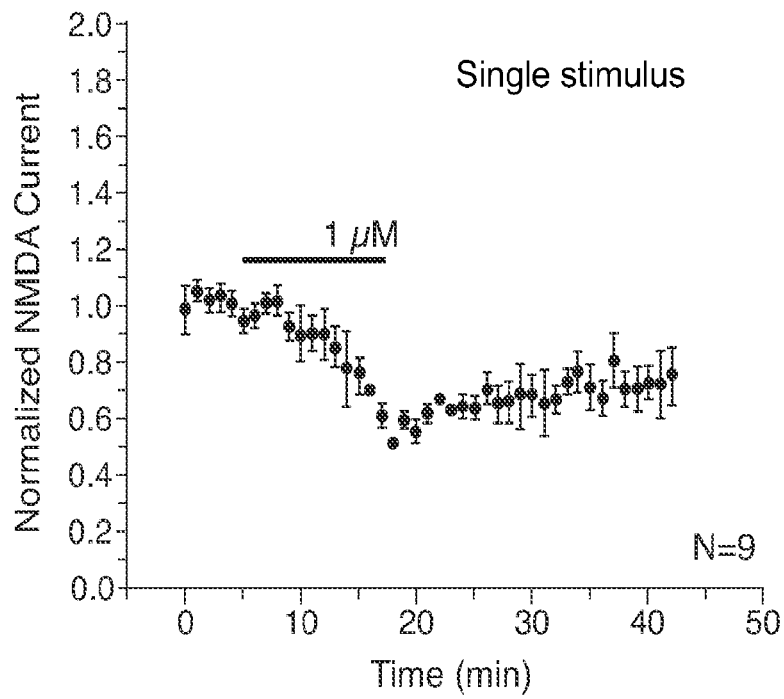
Figure 2D:
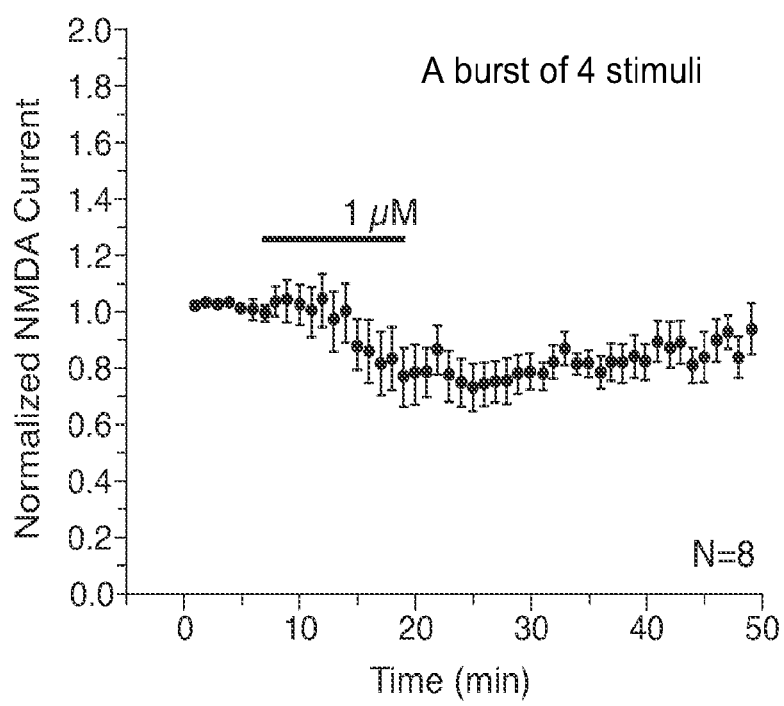
Figure 2E:
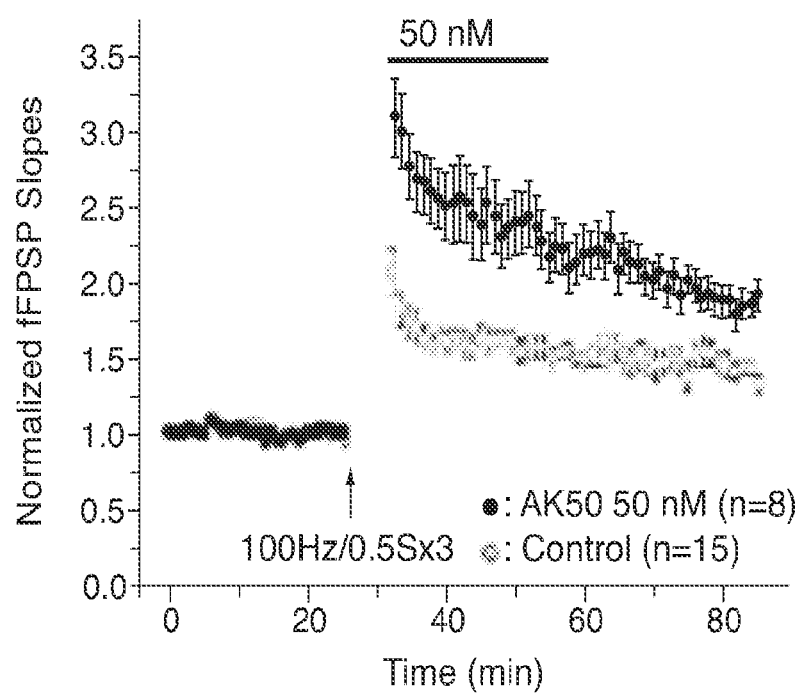

This disclosure is generally directed to compounds that are capable of modulating NMDA, e.g. NMDA antagonists or partial agonists, and compositions and/or methods of using the disclosed compounds.

The following definitions are used throughout the description of the present disclosure:

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl). Exemplary alkoxy groups include, but are not limited to, groups with an alkyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. Alkyl, alkenyl and alkynyl groups can optionally be substituted, if not indicated otherwise, with one or more groups selected from alkoxy, alkyl, cycloalkyl, amino, halogen, and —C(O)alkyl. In certain embodiments, the alkyl, alkenyl and alkynyl groups are not substituted, i.e., they are unsubstituted.

The term "alkynyl" as used herein refers to an unsaturated straight or branched hydrocarbon having at least one carbon-carbon triple bond. Exemplary alkynyl groups include, but are not limited to, ethynyl, propynyl, and butynyl.

The term "amide" or "amido" as used herein refers to a radical of the form —$R_aC(O)N(R_b)$—, —$R_aC(O)N(R_b)R_c$—, or —$C(O)NR_bR_c$, wherein $R_a$, $R_b$ and $R_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "carboxamido" refers to the structure —$C(O)NR_bR_c$.

The term "amine" or "amino" as used herein refers to a radical of the form —$NR_dR_e$, where $R_d$ and $R_e$ are independently selected from hydrogen, alkyl, alkenyl, alkynyl, aryl, arylalkyl, cycloalkyl, haloalkyl, heteroaryl, and heterocyclyl. The amino also may be cyclic, for example, $R_d$ and $R_e$ are joined together with the N to form a 3- to 12-membered ring, e.g., morpholino or piperidinyl. The term amino also includes the corresponding quaternary ammonium salt of any amino group, e.g., —$[N(Rd)(Re)(Rf)]+$. Exemplary amino groups include aminoalkyl groups, wherein at least one of $R_d$, $R_e$, or $R_f$ is an alkyl group. In certain embodiment, $R_d$ and $R_e$ are hydrogen or alkyl.

The terms "halo" or "halogen" or "Hal" as used herein refer to F, Cl, Br, or I. The term "haloalkyl" as used herein refers to an alkyl group substituted with one or more halogen atoms.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. The heterocyclic ring may be substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclic group is not substituted, i.e., the heterocyclic group is unsubstituted.

The term "heterocycloalkyl" is art-recognized and refers to a saturated heterocyclyl group as defined above. The term "heterocyclylalkoxy" as used herein refers to a heterocyclyl attached to an alkoxy group. The term "heterocyclyloxyalkyl" refers to a heterocyclyl attached to an oxygen (—O—), which is attached to an alkyl group.

The terms "hydroxy" and "hydroxyl" as used herein refers to the radical —OH.

"Pharmaceutically or pharmacologically acceptable" include molecular entities and compositions that do not produce an adverse, allergic or other untoward reaction when administered to an animal, or a human, as appropriate. "For human administration, preparations should meet sterility, pyrogenicity, general safety and purity standards as required by FDA Office of Biologics standards As used in the present disclosure, the term "partial NMDA receptor agonist" is defined as a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist.

As used herein "pharmaceutically acceptable carrier" or "exipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ⎓ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

As used in the present disclosure, "NMDA" is defined as N-methyl-d-aspartate.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in defined as that amount needed to give maximal enhancement of a behavior (for example, learning), physiological response (for example, LTP induction), or inhibition of neuropathic pain.

As used herein, "beta-turn motif" or beta-turn refers to a chemical structure having $C^\alpha$ (alpha carbon) atoms (a carbon atom next to a carbonyl carbon) substantially close, e.g. having a hydrogen bond between a donor and acceptor residue, where the donor and acceptor residue are separated by a distance that corresponds to the distance of two or three peptide bonds. A disclosed chemical structure has, for example, a beta-turn motif when the structure includes bicyclic rings (e.g., bicyclic spiro-lactam) that have restricted rotation, e.g., which may be evidenced by weak nOe (nuclear overhauser effect) spectra e.g., between H3 and H5 atoms.

Compounds

Compounds, e.g. peptide mimetics disclosed herein, in some embodiments are capable of binding to the NDMA ligand binding core of SEQ ID No. 1. For example, a disclosed peptide mimetic may have e.g. two alpha carbons that may be about 6 to about 14 Å, or about 9 to about 14 Å, or about 10 to about 13 Å apart. In some embodiments, a contemplated peptide mimetic may be internally constrained or conformally constrained so that it may, for example, mimic a biologically active conformation of a peptide. For example, a disclosed peptide mimetic may include a cyclic amide core, e.g. a bicyclic beta-lactam. For example, a disclosed peptide mimetic may be a disclosed compound having a two modular units (e.g., a bicyclic beta-lactam core), wherein each unit can be substituted with a naturally occurring amino acid.

For example, a disclosed compound may have a beta-turn motif that is stable upon administration to a patient, e.g. is substantially stable in-vivo or in an aqueous solution. In some embodiments, a disclosed compound may be capable of forming a hydrogen bond, or may be capable of binding to at least one, two, three or four amino acids of SEQ ID NO. 1, e.g. selected from the group consisting of PRO124, THR126, GLU178 and SER180.

A disclosed peptide mimetic may include a small synthetic (i.e. non-peptidyl) conformationally restricted component (e.g. a spirolactam moiety), which may for example, contribute to partial glycine site agonist activity of the compounds. For example, disclosed compounds include those represented by Formula I:

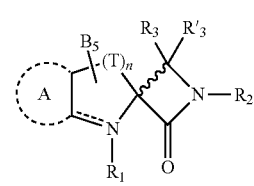

and pharmaceutically acceptable salts, stereoisomers, and N-oxides thereof; wherein T is, independently for each occurrence, $CR_4R_4'$, and n is 0, 1, 2 or 3;

A is optionally present and is selected from phenyl or pyridine, wherein A is optionally substituted by one or more substituents selected from $R_a$;

$R_1$ is selected from the group consisting of H, hydroxyl, —S(O)$_2$—C$_{1-4}$alkyl; —SO$_2$, C$_{1-4}$alkyl, C$_2$-C$_4$alkenyl, phenyl, $R_7$, or

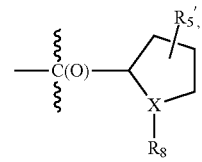

wherein C$_{1-4}$alkyl, C$_{2-4}$alkenyl, or phenyl is optionally substituted by one or more substituents selected from $R_a$;

X is CH or N;

$R_3$ and $R_3'$ are independently selected from the group consisting of H, halogen, hydroxyl, phenyl, C$_{1-4}$alkyl, amido, amine, or C$_{2-4}$alkenyl, wherein C$_{1-4}$alkyl, $C_{2-4}$alkenyl and phenyl are optionally substituted by one or more substituents selected from $R_a$;

$R_4$ and $R_4'$ are independently selected from the group consisting of H, halogen, hydroxyl, phenyl, $C_{1-4}$alkyl, amido, amine, $C_{1-4}$alkoxy or $C_{2-4}$alkenyl, wherein $C_{1-4}$alkyl, $C_{2-4}$alkenyl, $C_{1-4}$alkoxy, and phenyl are optionally substituted by one or more substituents selected from $R_a$;

$R_2$ is selected from the group consisting of H, $R_7$, $-S(O)_2$, $S(O)_2-C_1-C_4$alkyl, $C_{1-4}$alkyl, hydroxyl, or phenyl wherein $C_{1-4}$alkyl, $C_{2-4}$alkenyl and phenyl are optionally substituted by one or more substituents selected from $R_a$;

$R_5$ and $R_5'$ are each independently selected from group consisting of H, halogen, $C_{1-4}$-alkyl, $C_{1-4}$alkoxy, $C_{2-4}$alkenyl, cyano, amino, phenyl, and hydroxyl, wherein $C_{1-4}$alkyl, $C_{2-4}$alkenyl and phenyl are optionally substituted by one or more substituents selected from $R_a$;

$R_7$ is selected from group consisting of $-C(O)-R_9$, $-C(O)-O-R_9$, or $-C(O)-NR_d-R_9$, $R_9$ is selected from the group consisting of H, $C_{1-4}$alkyl, phenyl, or heterocyclic, wherein $C_{1-4}$alkyl, phenyl or heterocyclic is optionally substituted by 1, 2 or 3 substituents selected from $R_b$, $R_8$ is selected from group consisting of H, $-C(O)-C_{1-4}$alkyl or $C(O)-O-C_{1-4}$ alkyl, wherein $C_{1-4}$alkyl is optionally substituted by 1, 2 or 3 substituents selected from $R_a$;

$R_a$ is selected, independently for each occurrence, from carboxy, hydroxyl, halogen, amino, phenyl, $C_{1-4}$alkyl, and $C_{1-4}$alkoxy;

$R_b$ is selected, independently for each occurrence, from the group consisting of carboxy, hydroxyl, halogen, amino, phenyl, $C_{1-4}$alkyl, $C_{1-4}$alkoxy, and $-NH-R_c$;

$R_c$ is selected, independently for each occurrence from the group consisting of: $-C(O)-O-C_{1-4}$alkyl; and $-C(O)-C_{1-4}$alkyl; and $R_d$ is selected, independently for each occurrence, H and $C_{1-4}$alkyl;

and pharmaceutically acceptable salts, N-oxides or stereoisomers thereof.

For example, disclosed compounds may include those represented by:

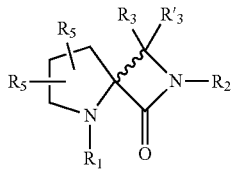

Ia wherein $R_1$ is $C(O)-C_{2-4}$alkyl, wherein $C_{2-4}$alkyl is substituted at one carbon with $NH_2$ or $-N$-carbobenzyloxy and at a different carbon by hydroxyl. For example, $R_1$ may be $C(O)-O-C_{1-4}$alkyl (e.g., methyl, ethyl, propyl, wherein $C_{1-4}$alkyl is substituted by phenyl, and $R_3$, $R_3'$, $R_5$ and $R_2$ are provided above.

In another embodiment, $R_1$ and $R_2$ of formula Ia may each independently be selected from an amino acid, e.g. a L- or D-isomer of an amino acid, e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and/or valine. For example, $R_1$ and $R_2$ may each be independently L-Thr or L-Ser, e.g. compounds such as:

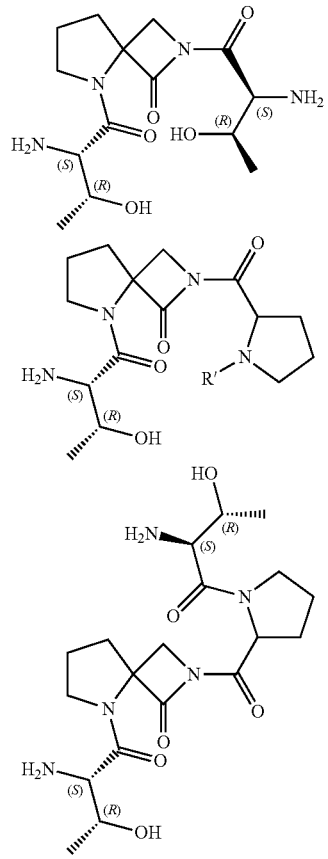

wherein R' is selected from the group consisting of H, or $C_{1-4}$alkyl.

In an embodiment, $R_1$ may be carbobenzyloxy, or may be represented by:

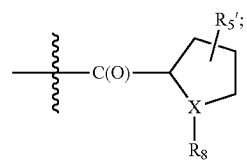

wherein X may be N; $R_5'$ may be H; and $R_8$ may be $-C(O)-C_{2-4}$alkyl (e.g. ethyl, propyl, n-butyl, or t-butyl), wherein $C_{2-4}$alkyl is substituted at one carbon with $NH_2$ or $-N$-carbobenzyloxy and at a different carbon by hydroxyl.

In certain embodiments, $R_3$ may be phenyl (optionally substituted as above), or may be H. $R_2$ may be, in some embodiments, a $-C(O)-C_{2-4}$alkyl, (e.g. ethyl, propyl, n-butyl, or t-butyl), optionally substituted at one carbon with $NH_2$ and another carbon with hydroxyl.

For any contemplated R-group that includes $C_{1-4}$alkyl (e.g. $R_1$, $R_3$, $R_5$), the alkyl may be selected from the group consisting of methyl, ethyl, propyl, n-butyl or t-butyl, and wherein said $C_{1-4}$alkyl is optionally substituted by one, two, or three substituents selected from the group consisting of F, Cl, or Br.

Such compounds may have differing isomerizations, and in some embodiments, may be represented by:

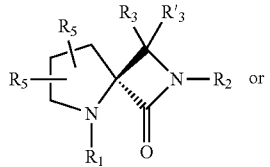

Ia

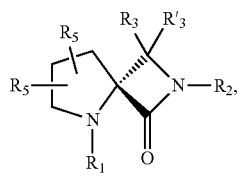

Ib and wherein $R_1$, $R_2$, $R_3$, $R'_3$, and $R_5$ may be as described above.

In another embodiment, compounds represented by formula II are contemplated:

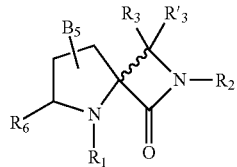

II and pharmaceutically acceptable salts, stereoisomers and N-oxides thereof; wherein $R_1$ is selected from the group consisting of H, hydroxyl, —S(O)$_2$—C$_{1-4}$alkyl; —SO$_2$, C$_{1-4}$alkyl; $R_7$, or

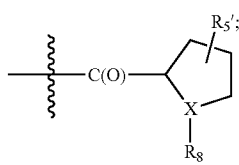

X is CH or N;

$R_3$ and $R_3'$ are each independently selected from the group consisting of H, halogen, hydroxyl, phenyl, C$_{1-4}$alkyl, amido, amine, or C$_{2-4}$alkenyl, wherein C$_{1-4}$alkyl, C$_{2-4}$alkenyl and phenyl are optionally substituted by one or more substituents selected from Ra;

$R_2$ is selected from the group consisting of H, $R_7$, —S(O)$_2$, S(O)$_2$—C$_{14}$alkyl, C$_{1-4}$alkyl, hydroxyl, or phenyl wherein C$_{1-4}$alkyl, C$_{2-4}$alkenyl and phenyl are optionally substituted by one or more substituents selected from R$_a$;

$R_5$ is selected from group consisting of H, halogen, C$_{1-4}$alkyl, C$_{1-4}$alkoxy, C$_{2-4}$ alkenyl, cyano, amino, phenyl, and hydroxyl, wherein C$_{1-4}$alkyl, C$_{2-4}$alkenyl and phenyl are optionally substituted by one or more substituents selected from R$_a$;

$R_6$ is selected from group consisting of H, halogen, C$_{1-4}$alkyl, C$_{1-4}$alkoxy, C$_{2-4}$alkenyl, cyano, amino, phenyl, and hydroxyl wherein C$_{1-4}$ alkyl, C$_{2-4}$alenyl and phenyl are optionally substituted by 1, 2 or 3 substituents selected from R$_a$;

$R_7$ is selected from group consisting of —C(O)—R$_9$, —C(O)—O—R$_9$, or —C(O)—NR$_d$—R$_9$, $R_9$ is selected from the group consisting of H, C$_{1-4}$alkyl, phenyl, or heterocyclic, wherein C$_{1-4}$alkyl, phenyl or heterocyclic is optionally substituted by 1, 2 or 3 substituents selected from R$_b$; or or $R_1$ and $R_6$, taken together with formula II form:

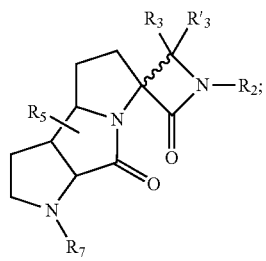

$R_8$ is selected from group consisting of H, —C(O)—C$_{1-4}$alkyl or C(O)—O—C$_{1-4}$alkyl, wherein C$_{1-4}$alkyl is optionally substituted by 1, 2 or 3 substituents selected from R$_a$;

$R_a$ is selected, independently for each occurrence, from carboxy, hydroxyl, halogen, amino, phenyl, C$_{1-4}$alkyl, and C$_{1-4}$alkoxy;

$R_b$ is selected, independently for each occurrence, from the group consisting of carboxy, hydroxyl, halogen, amino, phenyl, C$_{1-4}$alkyl, C$_{1-4}$alkoxy, and —NH—R$_c$;

$R_c$ is selected, independently for each occurrence, —C(O)—O—C$_{1-4}$alkyl; and —C(O)—C$_{1-4}$alkyl; and $R_d$ is H or C$_{1-4}$alkyl.

In an exemplary embodiment, the $R_1$ moiety of Formula I, II, Ia or Ib may be selected from the group consisting of:

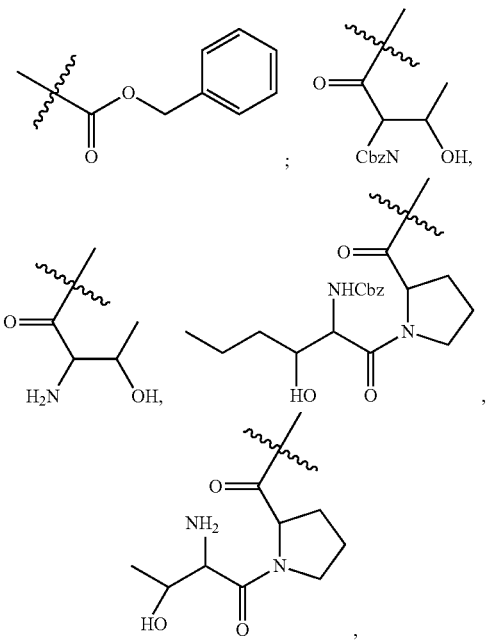

-continued
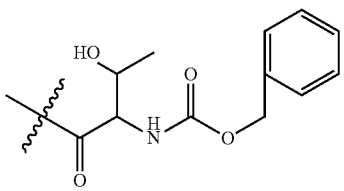
and
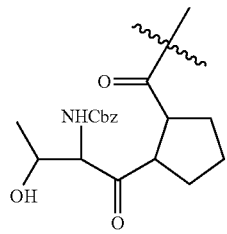
Exemplary compounds include
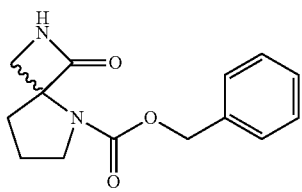
(compound B)
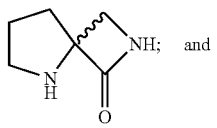
(AK-51)
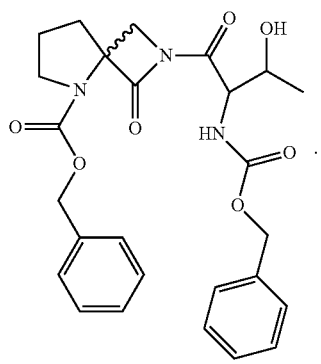
(AK-52)
Disclosed herein are compounds selected from the group consisting of:
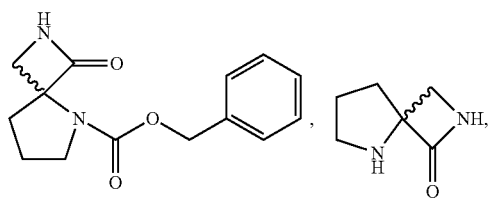
-continued
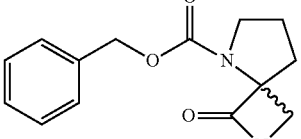
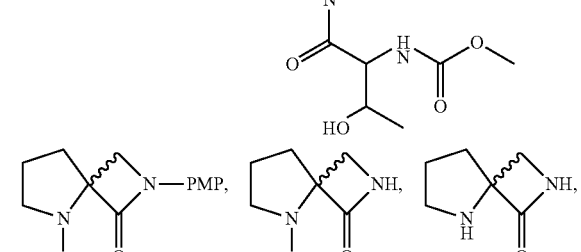
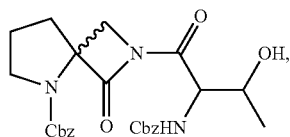
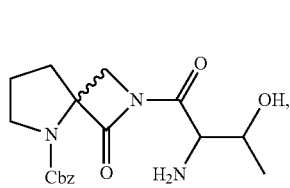
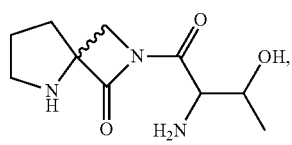
(AK55)
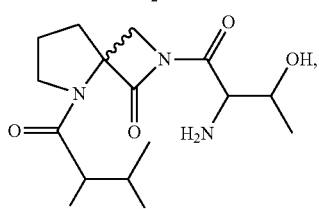
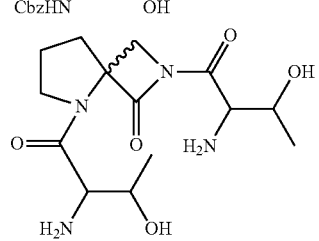
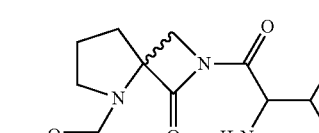
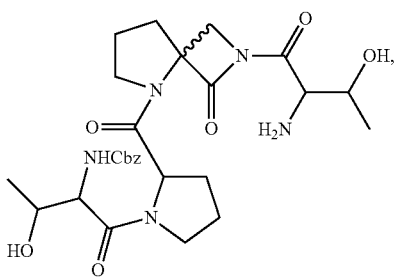

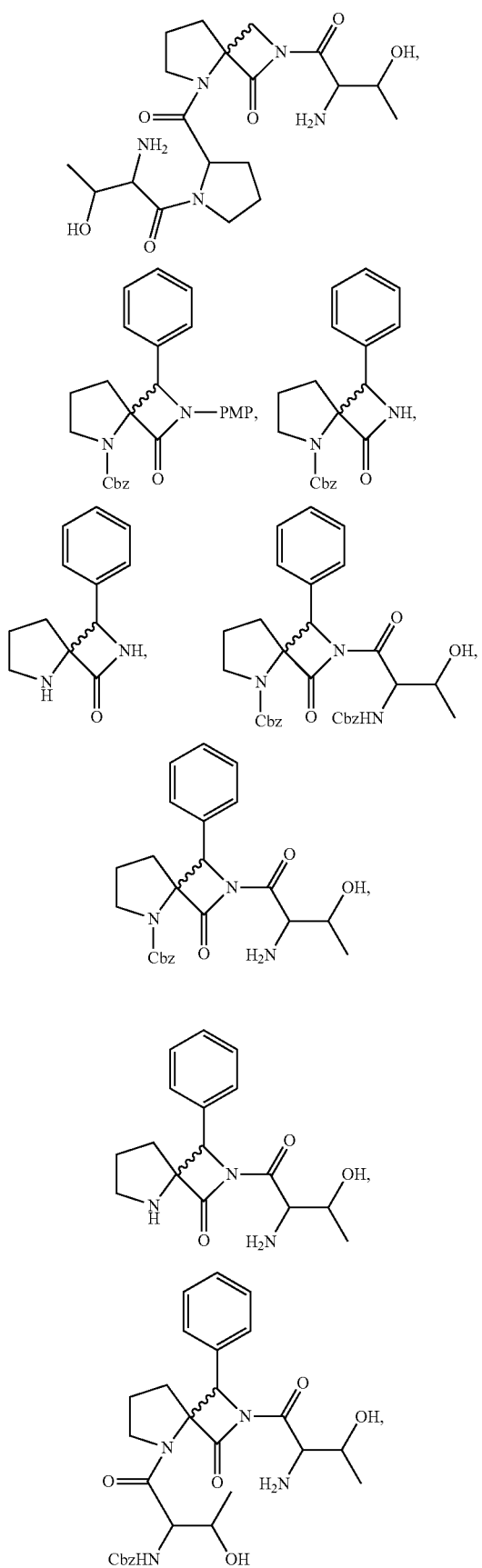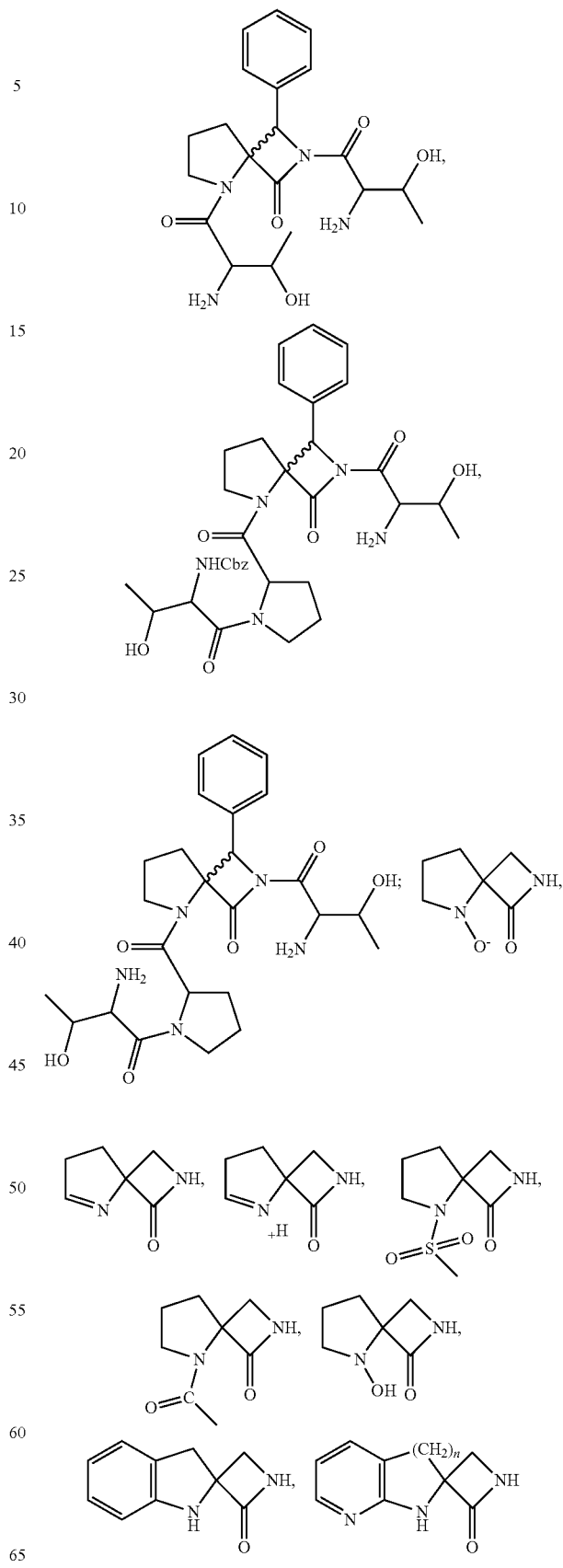

(where n is 0, 1, 2 or 3), and

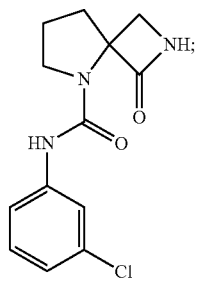 [SMILES: O=C(Nc1cccc(Cl)c1)N1CCCC12CNC2=O]

or pharmaceutically acceptable salts thereof.

and pharmaceutically acceptable salts, stereoisomers, or N-oxides thereof.

The compounds of the present disclosure and formulations thereof are intended to include both a D-isomeric form, an L-isomeric form, or a racemic mixture (both D- and L-isomeric forms) of any one or more of the compounds. In addition, the formulations of the compounds are intended to include any combination or ratio of L-isomeric forms to D-isomeric forms of one or more of the analogs described herein. These and other formulations of the disclosed compounds comprising a greater ratio of the D- and/or L-isomeric analog form may posses enhanced therapeutic characteristic relative to racemic formulations of a disclosed compounds or mixture of compounds. For example, disclosed compounds may be enantiomers, e.g.:

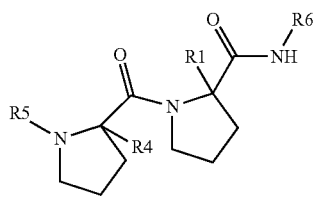

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

Other compounds contemplated herein include those having a cyclic amide core. Other exemplary compounds may be, in an embodiment, peptides, or in another embodiment, peptide mimetics. Contemplated compounds include those represented by:

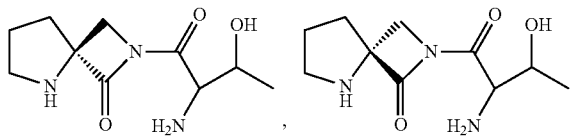

wherein,
$R_1$ is H or benzyl group;
$R_4$ is H or benzyl group;
$R_5$ is

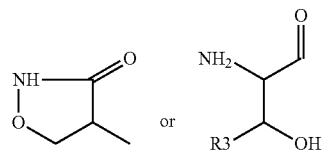

$R_6$ is

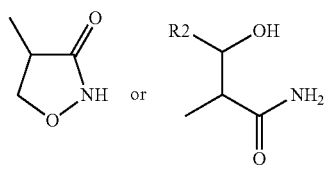

$R_2$ is H or $CH_3$;
$R_3$ is H or $CH_3$; and stereoisomers, or pharmaceutically acceptable salts or N-oxides thereof. Exemplary compounds include (SEQ ID NOS 2-3, respectively in order of appearance):

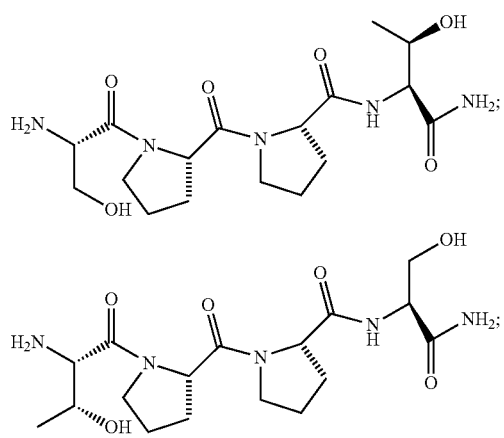

(SEQ ID NO: 4)

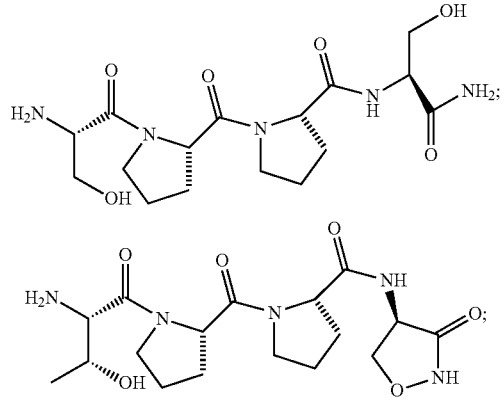

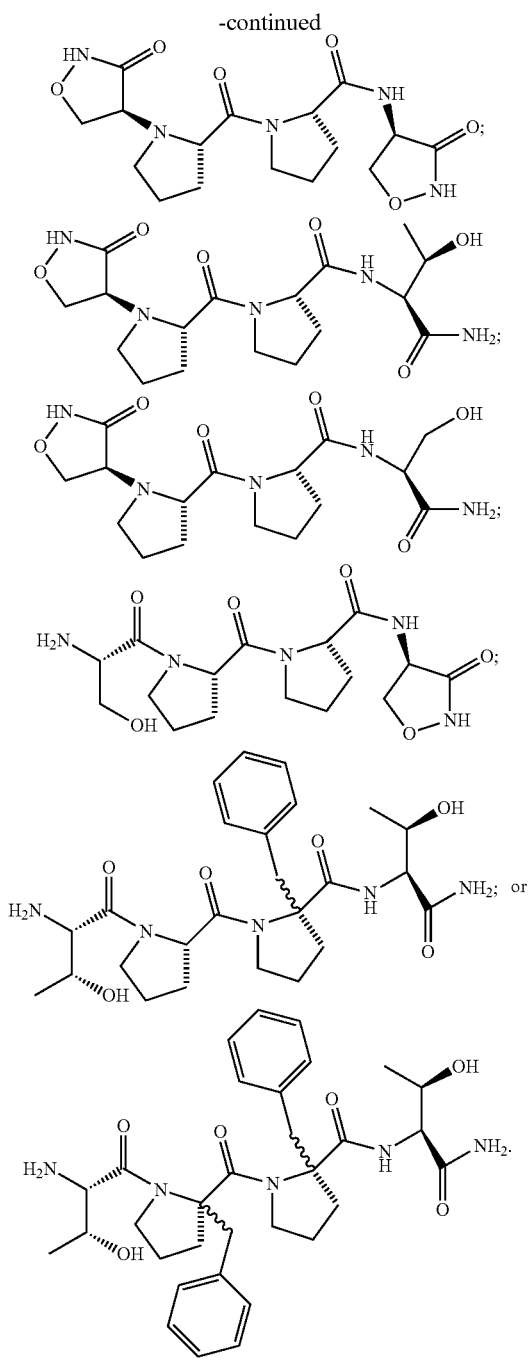

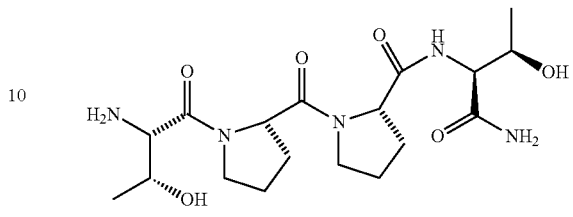

greater than the activity of existing NMDA receptor glycine site partial agonists. For example, disclosed compounds may possess a 10-fold to 20-fold enhanced potency compared to GLYX-13. GLYX-13 is represented by (SEQ ID NO: 5):

For example, provided herein are compounds that may be at least about 20-fold more potent as compared to GLYX-13, as measured by burst activated NMDA receptor-gated single neuron conductance ($I_{NMDA}$) in a culture of hippocampal CA1 pyramidal neurons at a concentration of 50 nM. In another embodiment, a provided compound may be capable of generating an enhanced single shock evoked NMDA receptor-gated single neuron conductance ($I_{NMDA}$) in hippocampal CA1 pyramidal neurons at concentrations of 100 nM to 1 µM. Disclosed compounds may have enhanced potency as compared to GLYX-13 as measured by magnitude of long term potentiation (LTP) at Schaffer collateral-CA-1 synapses in in vitro hippocampal slices.

Preparation of Compounds

In some embodiments, a disclosed compound, e.g. a peptide mimetic having a beta-turn motif capable of binding to the NMDA ligand binding core of SEQ ID NO 1, may be formed by incorporating one or more dehydro amino acids within a peptide. For example, peptides containing dehydrophenylalanine and/or dehydroleucine and/or alpha-aminobisobutyric acid may be incorporated to make a peptide mimetic having a beta-turn motif.

In another embodiment, a disclosed compound may be formed using a constrained bicyclic beta-turn dipeptide (BTD) motifs. This approach is based on the replacement of dipeptide component by incorporation of a carboxyl and an amino group in geometrically suitable positions for peptide coupling (see figure below) for inducing turns.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or

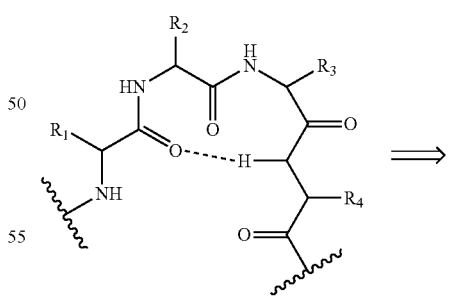

Typical beta turn

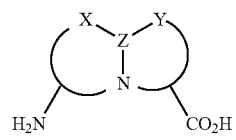

BTD motif

For example, a dipeptide component such as one or more azabicyclononanes may be incorporated to produce a structure having a beta-turn motif. In another example, a disclosed peptide mimetic may include a core structure as exemplified below, e.g. in place of two, three, or four amino acids:

In some embodiments, an azacycloalkeane may mimic a beta turn mimetic, e.g.:

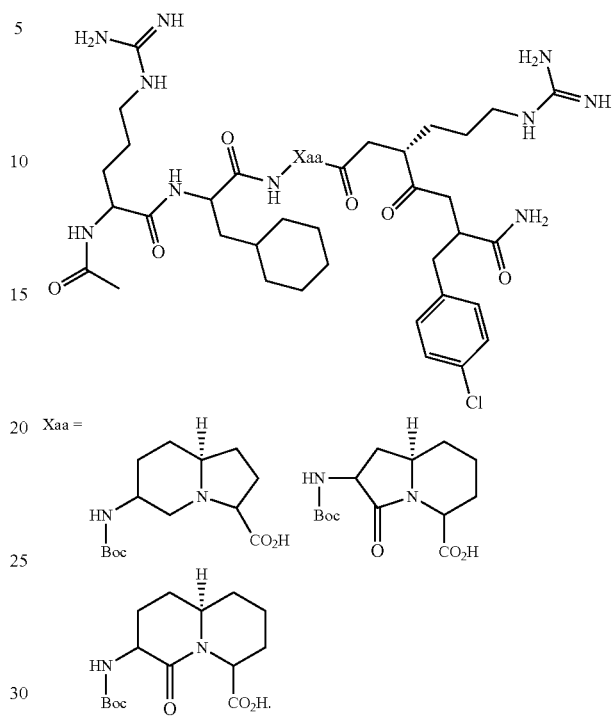

The following schemes are representative synthetic routes that may be used to prepare disclosed compounds and intermediates thereof.

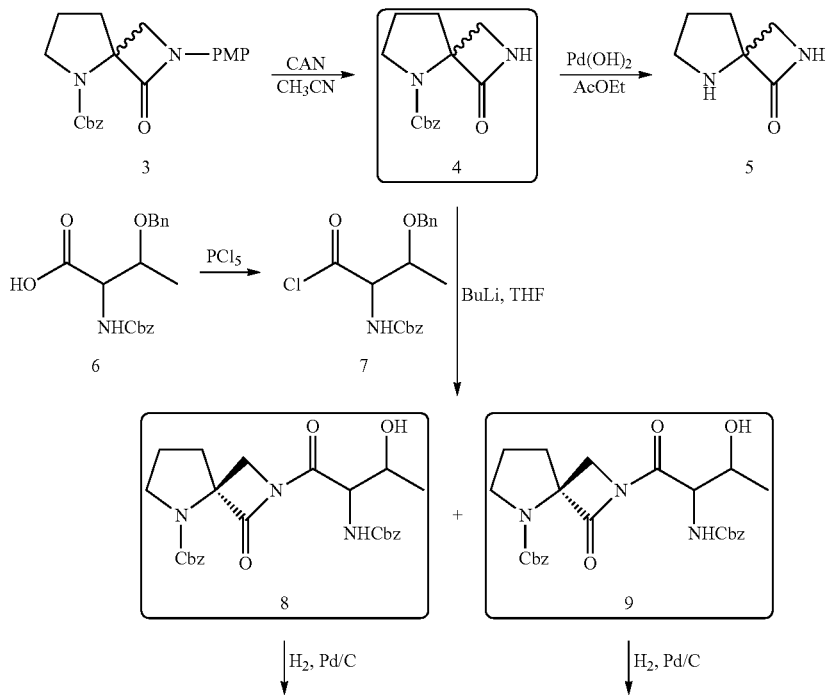

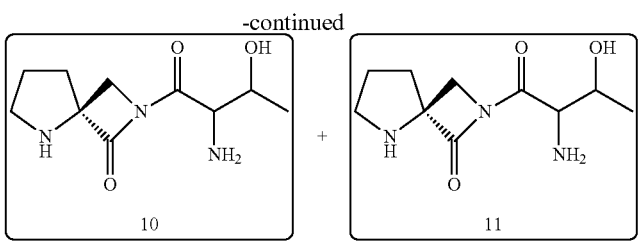

Scheme 2

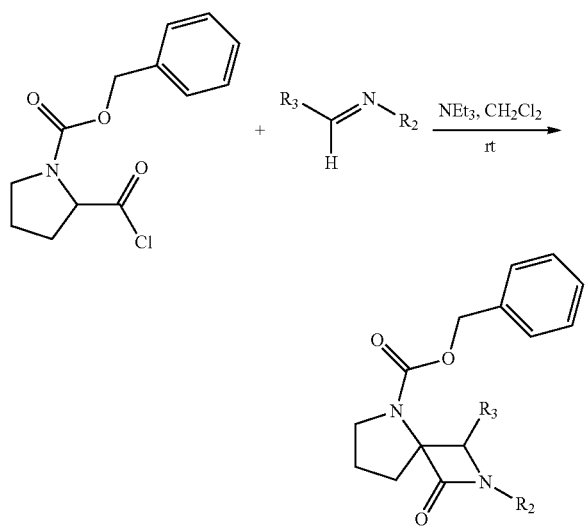

Ceric ammonium nitrate, or "CAN", is the chemical compound with the formula $(NH_4)_2Ce(NO_3)_6$. This orange-red, water-soluble salt is widely used as an oxidizing agent in organic synthesis. This compound is used as a standard oxidant in quantitative analysis.

PMP refers to p-methoxybenzylidene; Cbz refers to a carbobenzyloxy radical that can be depicted as:

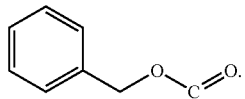

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

As used herein "pharmaceutically acceptable carrier" or "excipient" includes any and all Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound may be formulated with one or more additional compounds that enhance the solubility of the compound.
Methods Methods for treating cognitive disorders and for enhancing learning is provided. Such methods include administering a pharmaceutically acceptable formulation of one or more of the disclosed compounds to a patient in need thereof. Also contemplated are methods of treating patients suffering from, memory deficits associated with aging, schizophrenia, special learning disorders, seizures, post-stroke convulsions, brain ischemia, hypoglycemia, cardiac arrest, epilepsy, migraine, as well as Huntington's, Parkinson's and Alzheimer's disease.

Other methods contemplated include the treatment of cerebral ischemia, stroke, brain trauma, brain tumors, acute neuropathic pain, chronic neuropathic pain, sleep disorders, drug addiction, depression, certain vision disorders, ethanol withdrawal, anxiety, and memory and learning disabilities. In yet another aspect, a method for enhancing pain relief and for providing analgesia to an animal is provided

EXAMPLES

The following examples are provided for illustrative purposes only, and are not intended to limit the scope of the disclosure.

Example 1

Synthesis of Pyrrolidine-Derived Spiro β-Lactam Derivatives

The following reaction sequence was used (Scheme A) to synthesize Spiro Lactams. Hexahydro-1,3,5-triazines, Cbz-L-proline acid chloride and N-(Cbz) O-(benzylether)-L-threonine acid chloride as starting materials.

Scheme A:

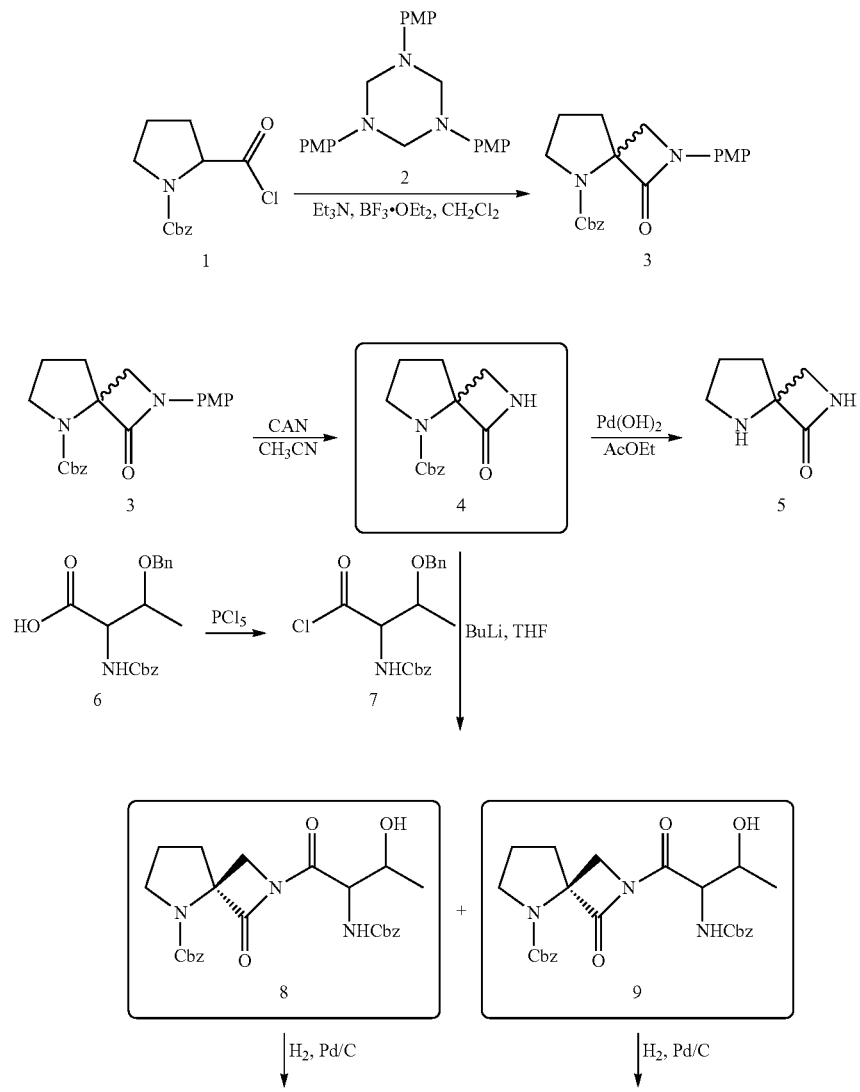

-continued

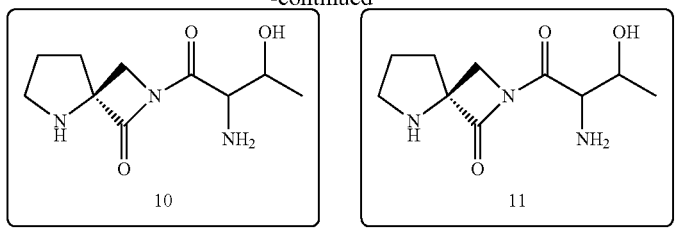

TABLE 1

| Lot # | Structure | Quantity | HPLC % Purity | Mass (M+ H) | HNMR |
|---|---|---|---|---|---|
| 4 | (pyrrolidine-azetidinone with CBZ) | 20 mg | 93 | 261 | YES |
| 5 (AK-51) | (pyrrolidine-azetidinone NH) | 150 mg | — | 127 | YES (>95% purity) |
| 8 | (spirolactam with CBZ and NHCBZ) | 17 mg | 73 | 496 | — |

Example 2

Synthesis of Compounds and Intermediates

Spiro Lactam 3. The synthesis of C4 unsubstituted spirolactam 3 was conducted via Staudinger reaction of methyleneimine derived from triazine 2. The [2+2]-cycle addition reaction between the ketene derived from Cbz-L-proline acid chloride and the methyleneimine was carried out in the following way: ketene was generated by dehydrochlorination of the acid chloride with triethylamine at −40° C. for 45 min, and then a dichloromethane solution of triazine 2 and boron trifluoride etherate (which depolymerize the triazine) was added. After 12 hours, the corresponding spirolactam 3 was obtained as a mixture of enantiomers, with 30 to 50% yield. The oxidative removal of the PMP group from spiro lactam 3 in the presence of CAN gave the N-unsubstituted derivative spirolactam 4, which upon treatment with Pd(OH)$_2$/C gave the corresponding spirolactam intermediates 5.

Spiro lactam 4 was obtained in 93% purity (HPLC) after purification by chromatography on silica gel. Spiro lactam 5 were obtained with purities >90% purity (by NMR) after chromatography on silica gel using gradient elution 20% to 70% Ethyl Acetate Cyclohexane, in 50% yield.

Example 3

Synthetic Routes to Intermediate Compounds

Triazine 2. To a solution of p-anisidine (24.6 g, 200 mmol.) in a mixture (500 mL) of ethyl acetate/water (1:1), cooled at 0° C., an aqueous solution (17 mL) of formaldehyde (37%) was added. The reaction mixture was stirred for 3 hours at 0° C. then 1 hour at room temperature, and the organic layer was separated, washed with water (50 mL), and dried over Na$_2$SO$_4$. The solvent was removed under vacuum, and a white solid was obtained. This solid was washed once with diethyl ether to provide 26.3 g (solid was dried at 40° C. overnight) of pure triazine 2 in 97% yield.

Spiro lactam Intermediates 3. To a stirred solution of the N-benzyloxycarbonyl L-proline acid chloride (5 g, 18.7 mmol.) in dry dichloromethane (65 mL) cooled to −40° C., was added dropwise dry triethylamine (10.4 mL, 74.7 mmol.). The solution became yellow to confirm that the ketene was formed.

After 45 min at −40° C., a purple solution of triazine 2 (2.52 g, 6.16 mmol.) and BF$_3$ OEt$_2$ (2.37 mL, 18.7 mmol.), previously mixed in CH$_2$Cl$_2$ (35 mL), was added dropwise. The mixture was allowed to warm slowly to room temperature overnight and then quenched with saturated aqueous NaHCO$_3$. The aqueous layer was extracted twice with CH$_2$Cl$_2$ (20 mL); the combined organic layers were washed with brine (20 mL) and dried over anhydrous Na$_2$SO$_4$. The solution was then concentrated and purified by column chromatography over silica gel using gradient elution 100%/cyclohexane to 20% ethyl acetate/cyclohexane to give 7.01 g of pure product with 37% yield.

Spiro lactam Intermediates 4. To a stirred solution of spirolactam 3 (2.4 g, 6.55 mmol.) in acetonitrile (49 mL) at −10° C., was added dropwise over 1 hour CAN (10.8 g, 19.6 mmol.), previously dissolved in H$_2$O (30 mL). After the addition was complete, the mixture was stirred for 45 min (TLC showed no remaining starting material). The reaction mixture was diluted with ethyl acetate (100 mL) and saturated NaHCO$_3$ (50 mL). To the organic layer was added water (100 mL) and solid sodium bisulfite (20 eq). The organic layer was washed with brine and dried over anhydrous Na$_2$SO$_4$. The solution was then concentrated and purified by column chromatography over silica gel using gradient elution 100%/cyclohexane to 50% ethyl acetate/cyclohexane to give 0.87 g of pure product in 50% yield.

Spiro lactam Intermediates 5 (AK-51). 0.5 g of 4 were dissolved in 20 mL of ethyl acetate and transferred via cannula to a flask under H2 (1 atm) containing 50 mg of 10% Pd(OH)$_2$—C catalyst. The mixture was stirred for overnight under H$_2$ at 50 PSi and then the catalyst was filtered off through celite. The organic layer was concentrated and purified by chromatography on silica gel to afford 120 mg of product in 50% yield.

N-(Cbz)-O-(benzyl ether)-L-threonine acid chloride 7. To a stirred solution of N-(Cbz)-O-(benzyl ether)-L-threonine (0.95 g, 2.7 mmol.) in dry ether (27 mL) was added PCl5 (0.61 g, 2.9 mmol.) and the mixture was stirred for 3 hours at room temperature. Then the solvent was removed with high vacuum at room temperature. Toluene was added and removed as above. The crude white solid was used without any purification for the coupling reaction.

Spiro lactams Intermediates 8 and 9. To a stirred solution of spirolactam 4 (200 mg, 0.76 mmol.) in dry THF (4 mL) at −78° C. was added BuLi (0.32 mL, 0.80 mmol. in hexane) dropwise. After addition was complete, the mixture was stirred at −78° C. for 1 hour. N-(Cbz)-O-(benzyl ether)-L-threonine acid chloride 7 in THF (4 mL) was added at −78° C. The mixture was stirred for overnight from −78° C. to room temperature.

The reaction mixture was quenched with saturated NH$_4$Cl (10 mL) and ethyl acetate (10 mL) was added. The water layer was extracted twice with ethyl acetate. The combined organic layers were dried with MgSO$_4$ and concentrated to give 0.44 g of crude product. The crude product was eluted through silica gel with a gradient from 100% CH$_2$Cl$_2$ to 2% MeOH/CH$_2$Cl$_2$ giving fractions that ranged in purity from 44% to 73%. This reaction was repeated on 0.28 g of spirolactam 4 and gave after chromatography fractions with purities that ranged from 50% to 73%.

Example 4

NMDA Receptor Binding Assay

Tissue Preparation:

Crude synaptic membranes were prepared from rat hippocampi or from rat forebrains (male Sprague-Dawley rats) and washed extensively to remove endogenous amino acids, as previously described by Ransom and Stec (1988). Briefly, the crude synaptic membranes were resuspended in 20 volumes of 5 mM Tris-HCl buffer, pH 7.4 (for use in [$^3$H]TCP-binding experiments), or in 20 volumes of 5 mM Tris-acetate buffer, pH 7.4 (for use in [$^3$H]glycine-binding studies) and homogenized using a Polytron (Virtis shear; Virtis, N.Y., U.S.A.). Membranes were then pelleted by centrifugation at 48,000 g for 20 min. This step was repeated twice and the homogenate was stored at −70° C. in the same buffer. Before each use, homogenates were thawed at room temperature, pelleted, and washed four additional times. For the [$^3$H]glycine experiment, the pellet was first incubated for 30 min at 25° C. in 5 mM Tris-acetate buffer containing 0.04% Triton X-100 and then washed four times by homogenization and centrifugation. The final washed membranes were resuspended at concentrations of 2-3 mg/ml in either 5 mM Tris-HCl buffer or 5 mM Tris-acetate buffer.

TCP binding assays: Measurements of specific [$^3$H]TCP binding were performed as described previously (Haring et al., 1986, 1987; Kloog et al., 1988a). Final reaction mixtures consisted of 50-100 μg of membrane protein in 200 μl of 5 mM Tris-HCl buffer and contained either [$^3$H]TCP, or [$^3$H] TCP and the appropriate concentration of NMDA-receptor ligands or mAbs. Reactions were initiated by the addition of the membranes to the reaction mixtures. Unless otherwise indicated, binding assays were performed under nonequilibrium conditions at 25° C. for 1 h. Nonspecific binding was determined in parallel samples containing 100 μM unlabeled PCP. Binding reactions were determined by filtration on Whatman GF/B glass filters that had been pretreated with 0.1% polyethyleneimine for 1 h.

The dissociation of [$^3$H]TCP from its membrane-binding site was measured after equilibrating the receptors with 20 nM [$^3$H]TCP for 120 min. The dissociation reaction was initiated by the addition of 100 μM unlabeled PCP in the presence and absence of NMDA-receptor ligands or mAb. Reactions were terminated immediately (zero time) and after incubation for the additional periods of time indicated.

The effects of the three compounds were examined on 1) NMDA receptor-gated single neuron conductance (I$_{NMDA}$) in hippocampal CAI pyramidal neurons and 2) the magnitude of long-term potentiation (LTP) and long term depression (LTD) at Schaffer collateral CA1 synapses, in in vitro hippocampal slices. GLYX-13 has been reported to exibit a low concentration (1-10 μM) enhancement of burst-activated I$_{NMDA}$ and LTP, while simultaneously reducing LTD and single pulse evoked I$_{NMDA}$. A hundred fold higher GLYX-13 concentration of 100 μM converted to reducing LTP and burst I$_{NMDA}$, and no longer affected LTD.

Compound B showed a 20-fold enhancement in potency compared to GLYX-13. 50 nM of this compound markedly enhanced both single shock (1A) and burst evoked (1B) I$_{NMDA}$, as well as doubling the magnitude of LTP (1E). In contrast, 1 μM NRX-10,050 significantly reduced both single shock (1C) and burst evoked ((ID) I$_{NMDA}$, reminiscent of 100 μM GLYX-13. (See FIG. 2).

Figure 3A:
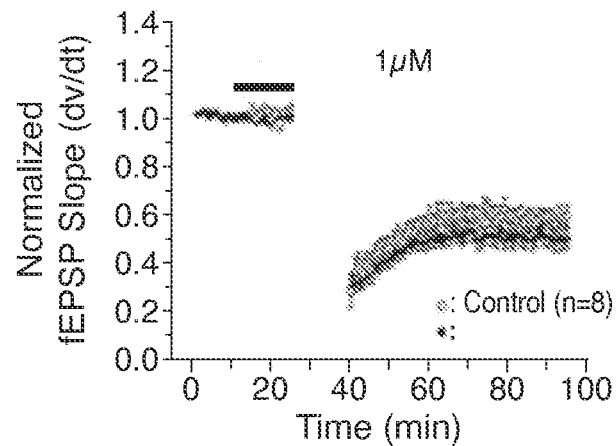
FIGS. 3A-3C demonstrate 100 nM and 1 µM concentrations of a disclosed compound (AK51) both enhance pharmacologically-isolated postsynaptic NMDA receptor-mediated (e.p.s.c.s.) at Shaffer collateral-CA1 synapse and potentiate LTP. 3A: Time course of the marked enhancement by NRX-10,051 (100 nM; solid bar) of single shock Schaffer collateral-evoked pharmacologically-isolated NMDA e.p.s.c.s recorded in CA1 pyramidal neurons (n=x). 3B: Time course of the enhancement by AK51 (1 µM; solid bar) of single shock Schaffer collateral-evoked pharmacologically-isolated NMDA e.p.s.c.s recorded in CA1 pyramidal neurons (n=y). 3C: Enhancement of high frequency (100 Hz/500 ms×3; solid arrow) Schaffer collateral stimulus-evoked LTP at synapses on CA1 pyramidal neurons by 100 nM ( ) and 1 µM (filled circles) AK5151, compared to control, untreated slices (open circles). 3D: Time course of LTD induced by a low frequency stimulus train (2 Hz/10 min; starting at arrow) at Schaffer collateral-CA1 synapses in slices pre-treated with 1 µM (filled circles; n=10) or 100 nM (filled diamonds; n=6 NRX-10,051, compared to control, untreated slices (open circles; n=8). Each point is the mean±EM of e.p.s.c. peNRX amplitude of n cells.).
Figure 3B:
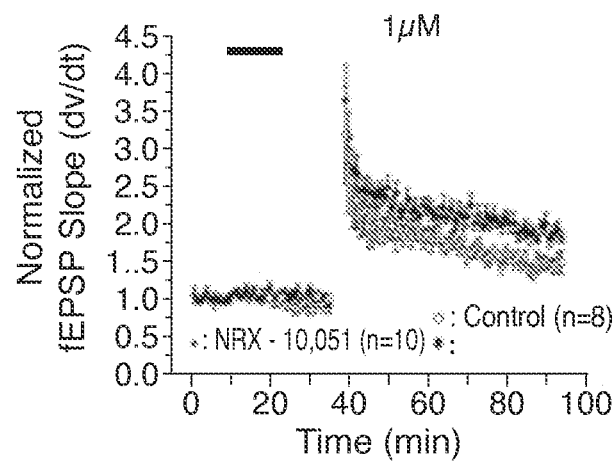
Figure 3C:
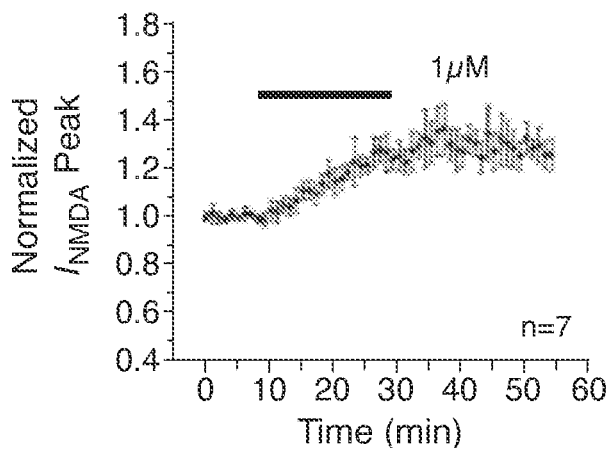
Figure 4A:
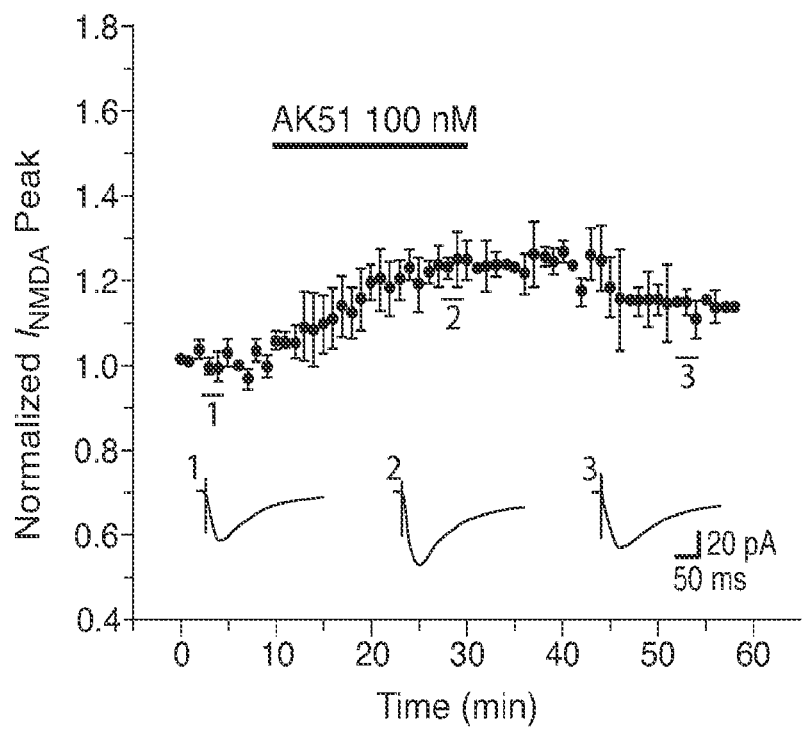
FIG. 4 indicates that a disclosed compound enhances NMDA current and LTP. A: Time course of effect of 20 min bath application of 100 nM AK51 (solid bar) on normalized pharmacologically-isolated NMDA receptor-gated current in CA1 pyramidal neurons under whole-cell recording (mean±SEM, n=5). B: Time course of effect of 20 min bath application of 1 µM AK51 (solid bar) on normalized pharmacologically-isolated NMDA receptor-gated current in CA1 pyramidal neurons under whole-cell recording (mean±SEM, n=6). C: Time course of effect of bath application of 100 nM AK51 (solid bar, filled circles, n=8) compared to untreated control slices (open circles, n=6) on the magnitude of long-term potentiation (LTP) of extracellular excitatory postsynaptic potential slope (mean±SEM, fEPSP) induced by high-frequency Schaffer collateral stimulation (arrow, 2×100 Hz/500 msec). D: Time course of effect of bath application of 1 µM AK51 (solid bar, filled circles, n=8) compared to untreated control slices (open circles, n=6) on the magnitude of LTP of fEPSP slope (mean±SEM) induced by high-frequency Schaffer collateral stimulation (arrow, 2×100 Hz/500 msec). E: Time course of effect of bath application of 1 µM AK51 (solid bar, filled circles, n=10) compared to untreated control slices (open circles, n=8) on the magnitude of long-term depression of fEPSP slope (mean±SEM) induced by low-frequency Schaffer collateral stimulation (arrow, 2 Hz/10 min)
Figure 4B:
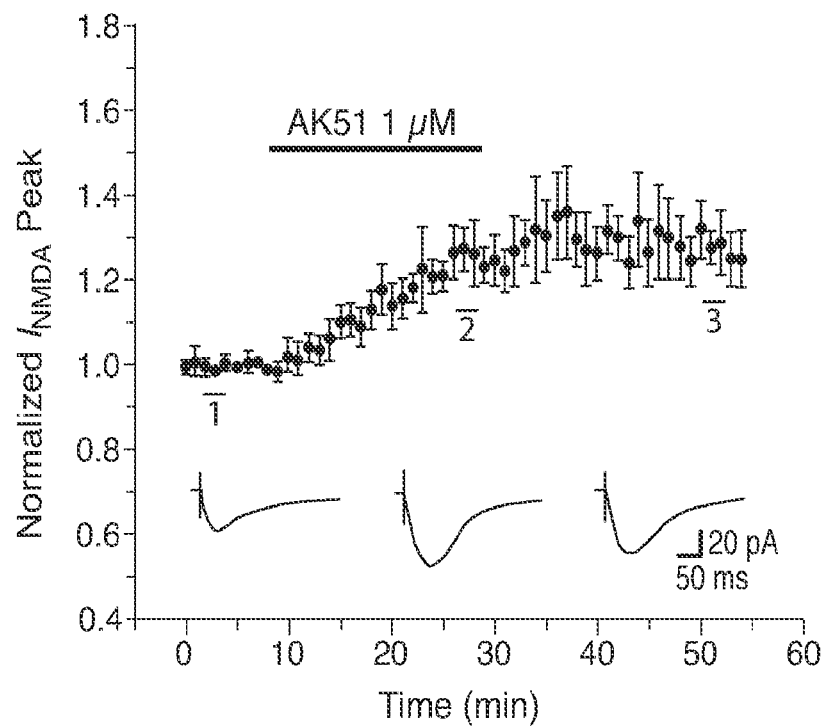
Figure 4C:
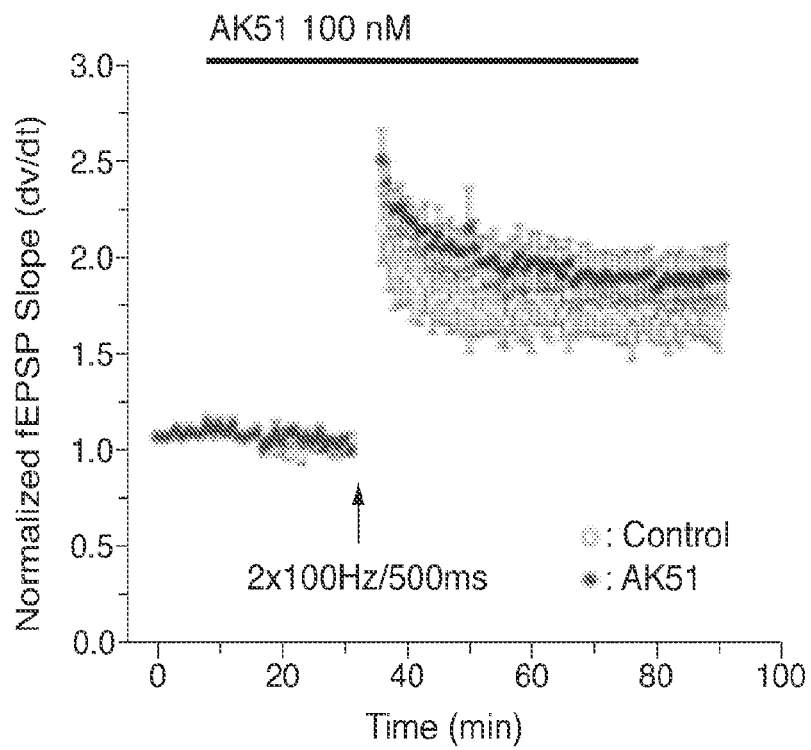
Figure 4D:
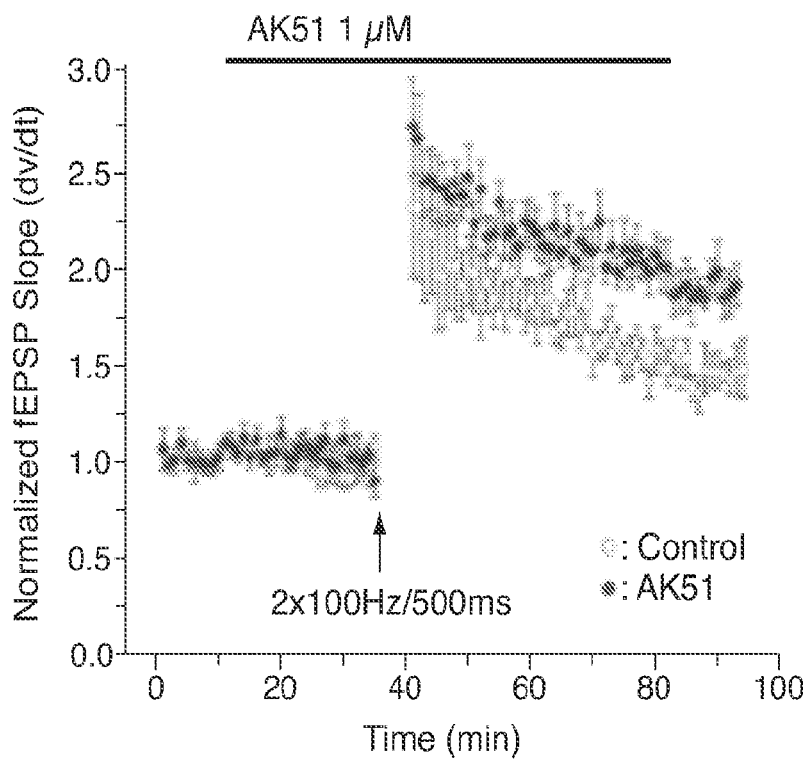
Figure 4E:
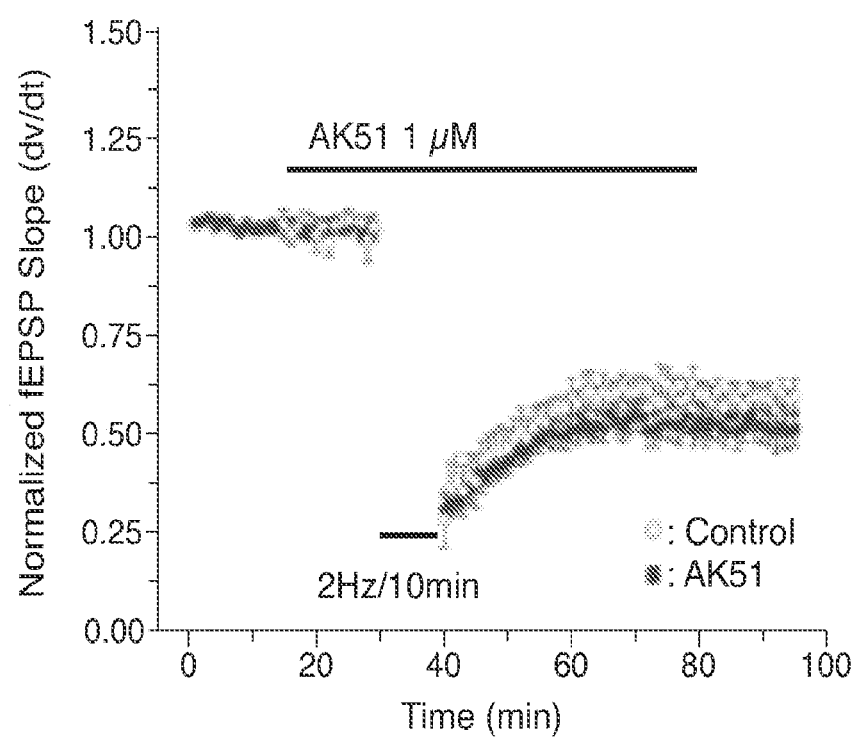

AK-51 exhibited less potency than compound B, but a wider concentration range in its stimulatory actions (FIG. 3). Both 100 nM (2A) and 1 μM NRX-10,051 enhanced single-shock evoked I$_{NMDA}$, while 1 uM NRX-10,051 doubled the magnitude of LTP (2D), while not altering LTD (2E).

AK-52 produced only a mild enhancement of single-shock evoked I$_{NMDA}$ at a low concentration (100 nM; 3A), which converted to significant reduction in I$_{NMDA}$ at a 1 uM concentration (3B). 100 nM AK-52 produced an enhancement of LTP similar in magnitude to compound B and AK-51, but this converted to a slight, but significant, reduction in LTP at the 1 μM concentration, without altering LTD.

These three compound showed about a 20-fold enhancement in potency compared to GLYX-13. Compound B is the most potent enhancer of I$_{NMDA}$ at low concentrations (50 nM). While AK-51 enhancement of I$_{NMDA}$ was smaller in magnitude, this effect remained when the AK-51 was increased 10-fold (100 nM to 1 μM). The AK-52 was the weakest enhancer of I$_{NMDA}$, and this effect reversed more quickly to a frank reduction in I$_{NMDA}$.

These compounds enhanced the magnitude of LTP to similar extents, approximately to a doubling. GLYX-13 was the only compound that could simultaneously increase LTP and reduce LTD: AK-52 did not affect LTD, even at a concentration that reduced I$_{NMDA}$. GLYX-13 can selectively enhance $I_{NMDA}$ mediated by NMDA receptors containing NR2A/B subunits, and these receptors are localized to extrasynaptic loci and are more strongly activated by neuronal bursts that induce LTP. While all of the tested compounds have potent effects on LTP and $I_{NMDA}$, the lesser effects on LTD suggest that they have increased selectivity for NR2A/B containing NMDA receptor glycine sites than the GLYX-13.

Example 5

T-Maze Learning Model

Male 3 month old Fisher 344 X Brown Norway F1 cross rats (FBNF1) were used for this study. The t-maze was constructed with arms (45 cm long×10 cm wide×10 cm high) made of black Plexiglas enclosing the maze. Two plastic bottle caps, lined with wire mesh, were secured to the end of each goal arm in which the food reward (Cheerios, 100 mg/piece) was placed. Before the start of training, animals were gradually deprived of food to approximately 85% of their free feeding weight. On three successive days before the start of training, animals were habituated to the t-maze with food located throughout the maze. On the first day of training, animals were rewarded for right arm choices and were trained to a criterion of 9 out of 10 consecutive correct choices. On the second day of training, animals were rewarded for left arm choices, and were trained to a criterion of 9 out of 10 consecutive correct choices. On the subsequent testing day, animals were given injections of AK51 (0.3, 1, 3, 10, 30 mg/kg p.o.), or DMSO vehicle (1 mg/ml; Sigma, Saint Louis Mo.) in a blind manner via gastric gavage (4", 16-ga; Braintree Scientific, Braintree Mass) 60 min prior to the start of testing (n=8-9 per group. On the first trial of testing, both arms were baited with food and for the subsequent 20 trials only alternating choices (opposite of the animal's previous choice) were rewarded (~30 sec inter-trial interval). The number of trials to criterion (5 consecutive correct choices) was calculated for each animal. Data was analyzed by ANOVA followed by Fisher PLSD post hoc tests comparing individual drug doses to vehicle ($\alpha$=0.05).

Figure 5:
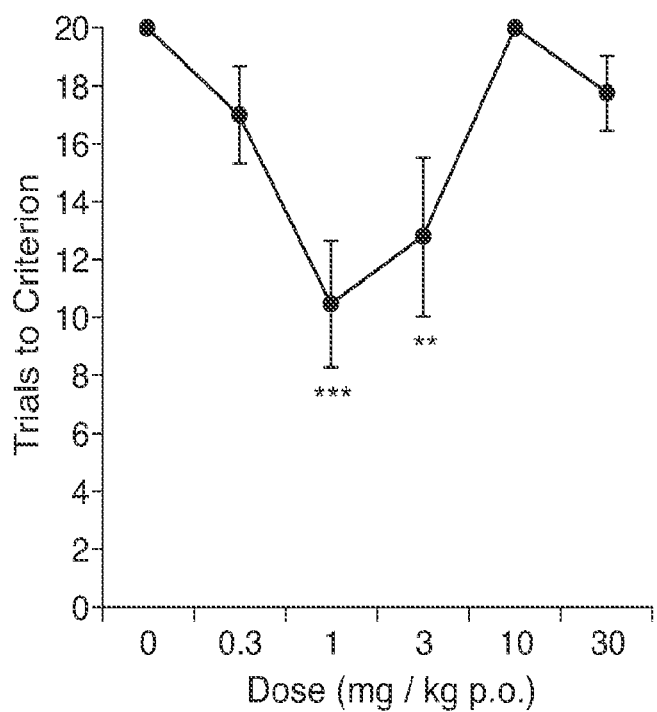
FIG. 5 depicts the results of a T-maze test in rats using a disclosed compound.

FIG. 5 depicts mean (±SEM) trials to criterion in the alternating T-maze task (20 trials) in food deprived 3 month old rats. Animals were injected p.o. with 0, 0.3, 1, 3, 10, or mg/kg AK051 in DMSO vehicle (n=8-9 per group) 60 min before the start of testing. *P<0.001, P<0.01, Fisher PLSD post hoc vs. vehicle Example 6

Formalin Test of Neuropathic Pain

Figure 6:
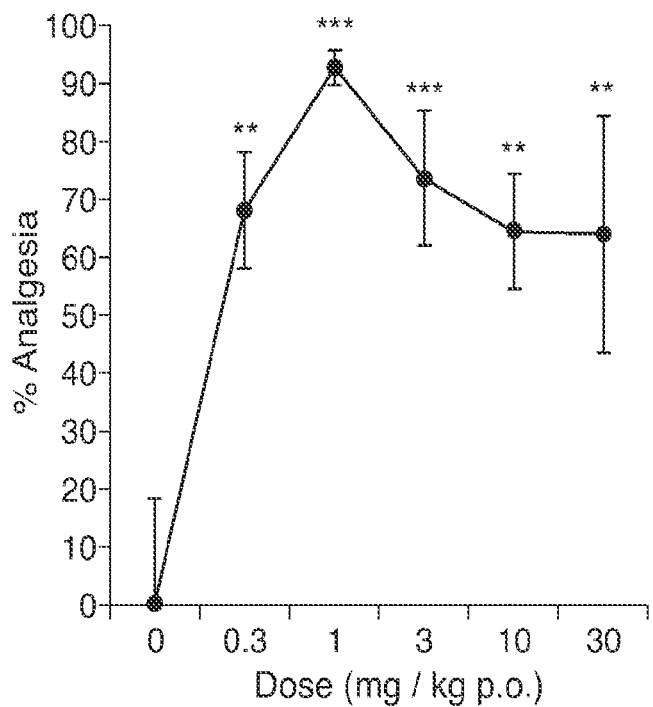
FIG. 6 depicts the results of a formalin neuropathic pain assay in rats.

Experiments were conducted as previously described (Abbott et al. Pain, 60, 91-102, 1995; Wood et al., *Neuroreport*, 19, 1059-1061 2008). Male 3 month old Fisher 344 X Brown Norway F1 cross rats (FBNF1) were used for this study. Before the start of testing, animals were habituated to the testing chamber (30×30×60 cm opaque plexiglass) for 10 min each day over 2 consecutive days. On the testing day, animals were given injections of AK51 (0.3, 1, 3, 10, 30 mg/kg p.o.), or DMSO vehicle (1 mg/ml; Sigma, Saint Louis Mo.) in a blind manner via gastric gavage (4", 16-ga; Braintree Scientific, Braintree Mass.) 60 min prior to formalin injections (n=8-9 per group). Animals were placed into the testing chamber 10 min prior to formalin injection. For the formalin injection, rats were manually restrained and given a subcutaneous injection of 1.5% formalin (50 µL with a 26-ga needle; Sigma, Saint Louis Mo.) into the lateral footpad on the plantar surface of the left hind paw. After formalin injections rats were placed back into the testing chambers. Animals were videotaped from below with the aid of an angled mirror for 50 min post formalin injection. Total time spent licking the injected paw and total number of injected paw flinches during the late phase (30-50 min post formalin injection) were quantified off-line in a blind manner by a trained experimenter with high (r>0.9) inter- and intra-rater reliability for both measures. All animals were euthanized by $CO_2$ immediately after testing. Data was analyzed by ANOVA followed by Fisher PLSD post hoc tests comparing individual drug doses to vehicle ($\alpha$=0.05). FIG. 6 depicts mean (±SEM) % Analgesia defined as % reduction in flinches in the late phase response (30-50 min) after intraplantar formalin injection (50 µL of 1.5% formalin).

Example 7

Oral Formulations Enhancing Learning and Memory

An oral preparation of AK-51, was prepared in dimethylsulfoxide (DMSO). All doses were administered in a volume of 300 µl. The animals were then fed p.o. by gavage (force fed by mouth with an inserted feeding needle) a volume calculated to deliver to the animal a defined dose based on body weight as follows 0.0 mg/kg 300 µL DMSO (vehicle); 0.3 mg/kg, 300 µL in DMSO; 1.0 mg/kg, 300 µL in DMSO; 3.0 mg/kg, 300 µL in DMSO; 10.0 mg/kg, 300 µL in DMSO; 30.0 mg/kg, 300 µL in DMSO.

Animals were injected 60 minutes before the start of testing with one of the dose amounts recited above. Then, an alternating T-maze task (20 trials) was used to asses learning behavior in the animals. This protocol is described at Example 5. Briefly, the T-maze is a choice task. The subject rat was placed in the base of the "T". Following a short delay, it was allowed to explore the maze and choose to enter either the right or left arms. The choice is scored according to variety of criterion, including spontaneous alternation, cued reward, or to indicate a preference. Based on the criterion used in this study, the T-maze was used to test learning and memory. Food placed at one end of the maze was used as the positive reinforcer for each animal test.

Animals given a 1.0 mg/kg dose by mouth of AK-51 demonstrated a statistically significant enhancement of learning behavior in the T-maze test (P<0.001). Animals given a 3.0 mg/kg dose by mouth of the non-peptide analog NRX-10,051 also demonstrated a statistically significant enhancement of learning behavior in the T-maze test (P<0.01).

Example 8

Isomers

Figure 7A:
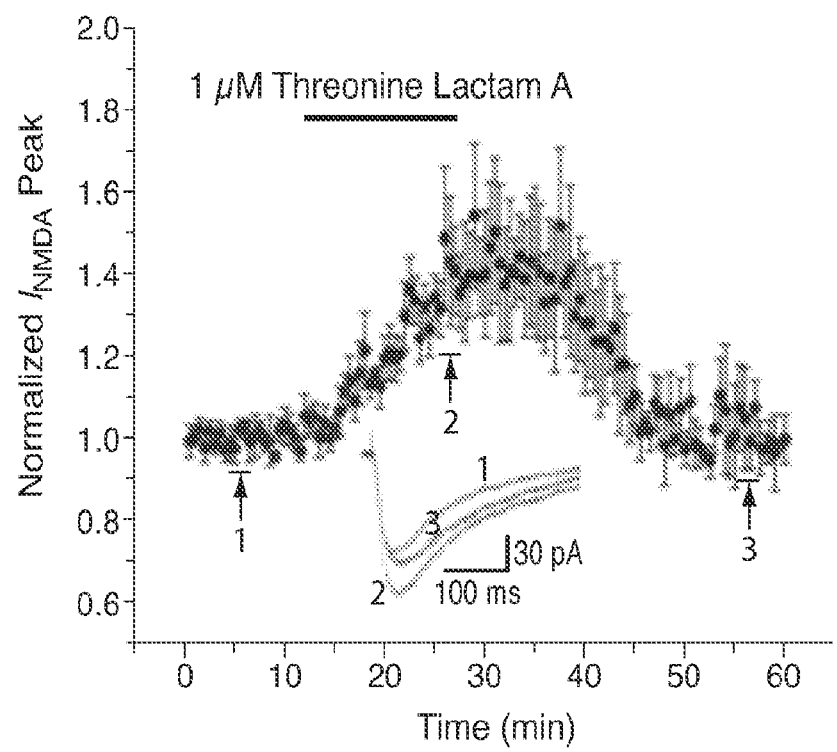
FIG. 7 indicates that one isomer of a disclosed compound AK-55-A potently enhances NMDA current and LTP, while AK-55-B does not.
Figure 7B:
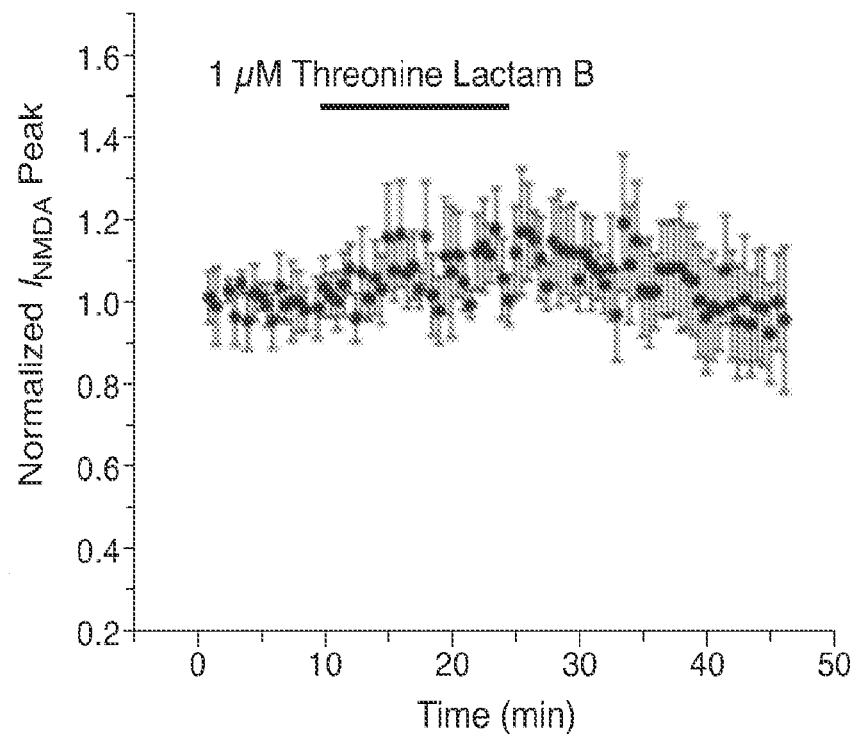
Figure 7C:
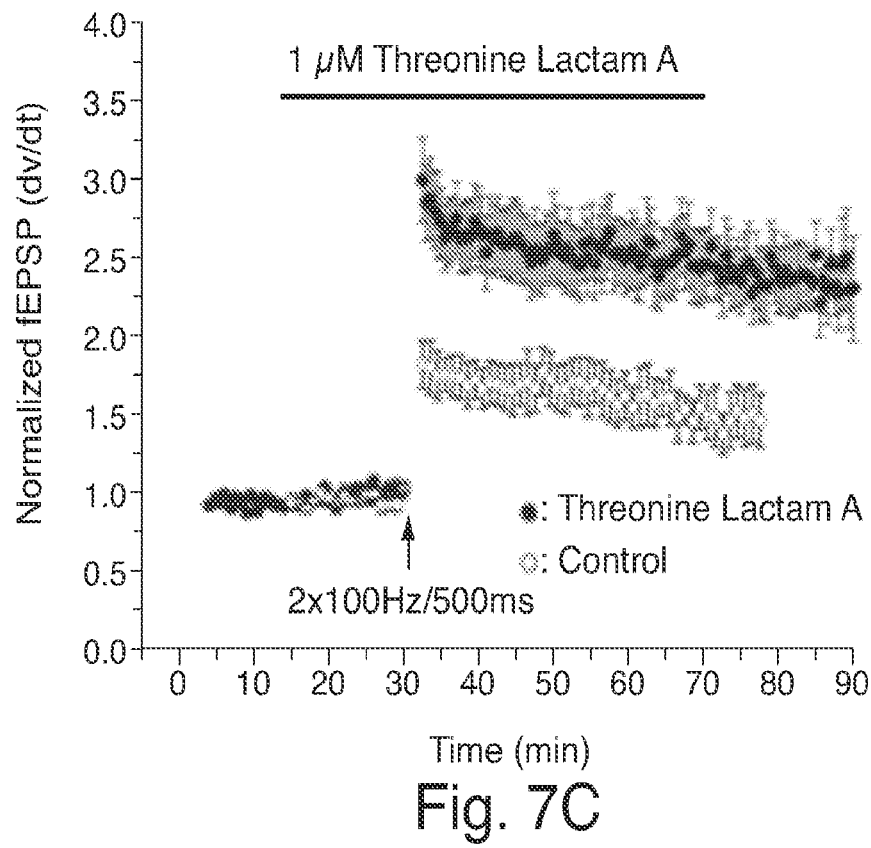
Figure 8:
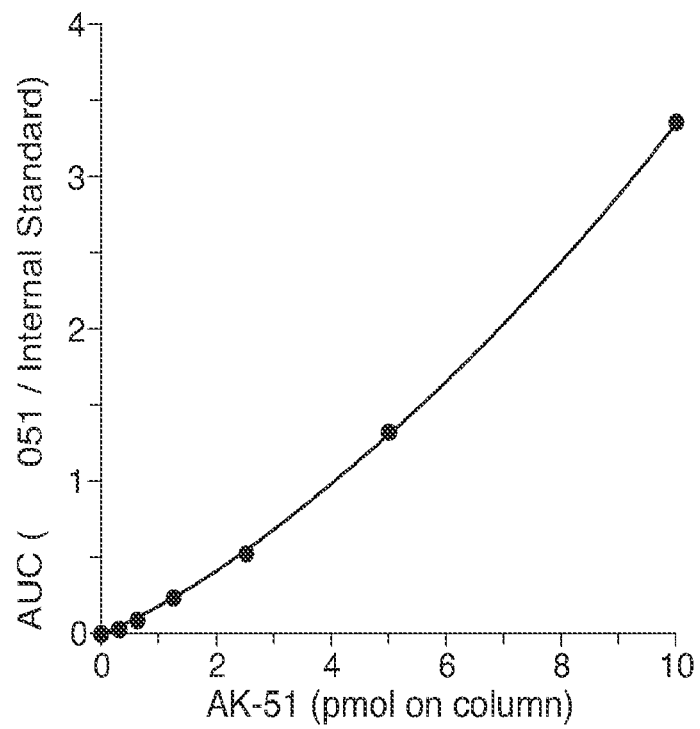
FIG. 8 depicts quantification by GC/MS and shows the area under the curve for AK-51 and [2H7]proline internal standard and was analyzed with GC/MS by selective ion monitoring following TBDMS derivatization based on methods adapted from Wood et al. Journal of Chromatography B, 831, 313-9 (2005). The quantitative range of the assay for this compound was 0.312 pmol to 10 pmol column. The ions utilized for SIM were 241.2 (this compound) and 350.3 (deuterated proline). $R^2=0.9998$ (Quadratic non-liner regression).
Figure 10:
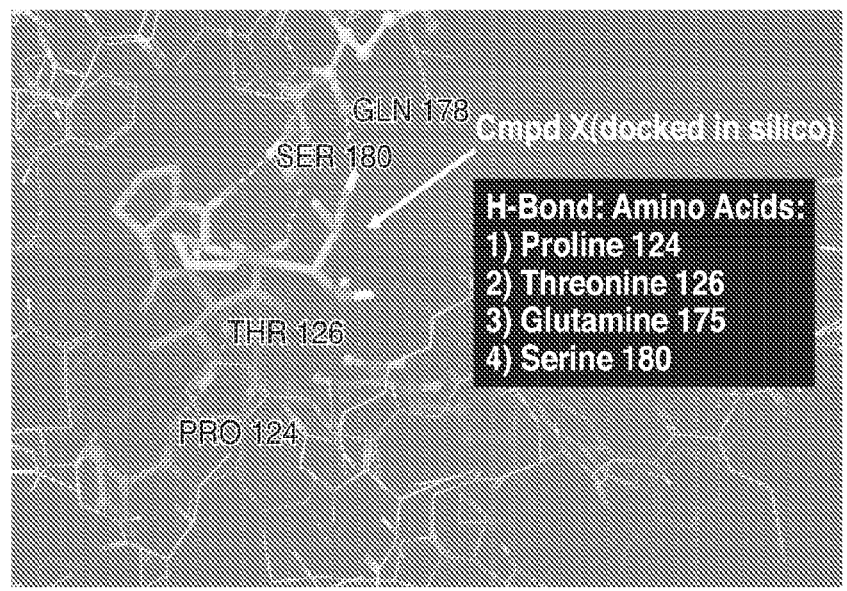
FIG. 10 depicts the crystal structure of compound X (GLYX-13) with the NMDA receptor NR1.
Figure 11:
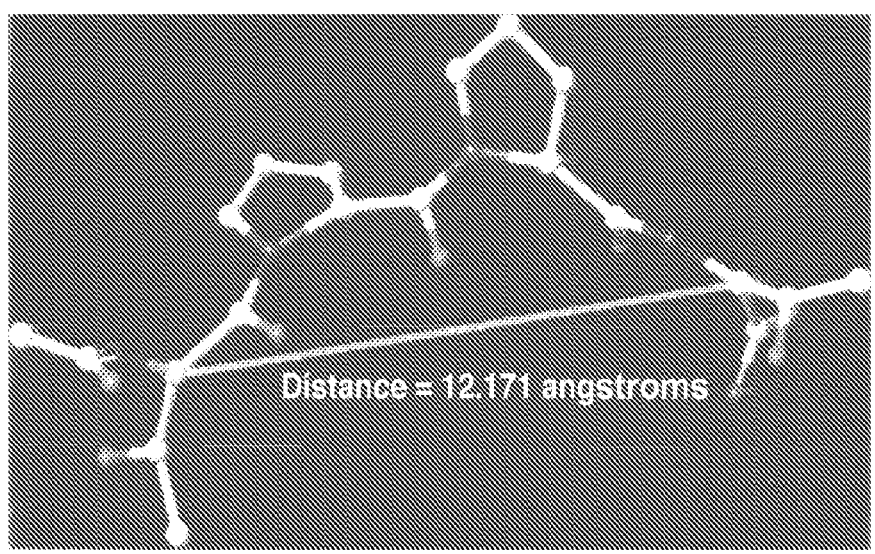
FIG. 11 depicts a model peptide (GLYX-13) that has a distance of 12.171 Å between alpha carbons.

The two different isomers of AK-55 was used in a NDMA binding assay as in Example 4. One isomer of AK-55 potently enhances NMDA while the other does not. FIG. 7A indicates the time course of effect of 15 min bath application of 1 µM AK55 (solid bar) on normalized pharmacologically-isolated NMDA receptor-gated current in CA1 pyramidal neurons under whole-cell recording (mean±SEM, n=6). B: Time course of effect of 15 min bath application of 1 µM AK55 (solid bar) on normalized pharmacologically-isolated NMDA receptor-gated current in CA1 pyramidal neurons under whole-cell recording (mean±SEM, n=7). C: Time course of effect of bath application of 1 µM AK6 (solid bar, filled circles, n=8) compared to untreated control slices (open circles, n=8) on the magnitude of long-term potentiation (LTP) of extracellular excitatory postsynaptic potential slope (mean±SEM fEPSP) induced by high-frequency Schaffer collateral stimulation (2×100 Hz/500 msec).

Example 9

Biochemical Assays

Table B depicts the results of binding assays against various targets with AK51:

TABLE B

| Target | Species | Concentration | % Inhibition |
| --- | --- | --- | --- |
| Glutamate, AMPA | rat | 10 μM | −8 |
| Glutamate, Kainate | rat | 10 μM | −13 |
| Glutamate, Metabotropic, mGlu$_5$ | human | 10 μM | −7 |
| Glutamate, NMDA, Agonism | rat | 10 μM | 27 |
| Glutamate, NMDA, Glycine | rat | 10 μM | −6 |
| Glutamate, NMDA, Phencyclidine | rat | 10 μM | −5 |
| Glutamate, NMDA, Polyamine | rat | 10 μM | −14 |
| Glutamate, Non-Selective | rat | 10 μM | −10 |
| Glycine, Strychnine-Sensitive | rat | 10 μM | 4 |
| Potassium Channel hERG | human | 10 μM | 3 |

Example 10

Identification of β Turn in Spiro Compounds

Proton 1-D experiments $^1$H, $^{13}$C, DEPT, homo nuclear 2-D experiments (DQF-COSY, TOCSY, NOESY) and Hetero nuclear experiments HSQC and HMBC in DMSO-D$_6$ at 30 degree Celsius are conducted to confirm the exact carbon chemical shifts and protons chemical shifts of the spiro compound:

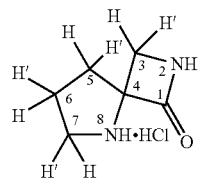

Figure 12:
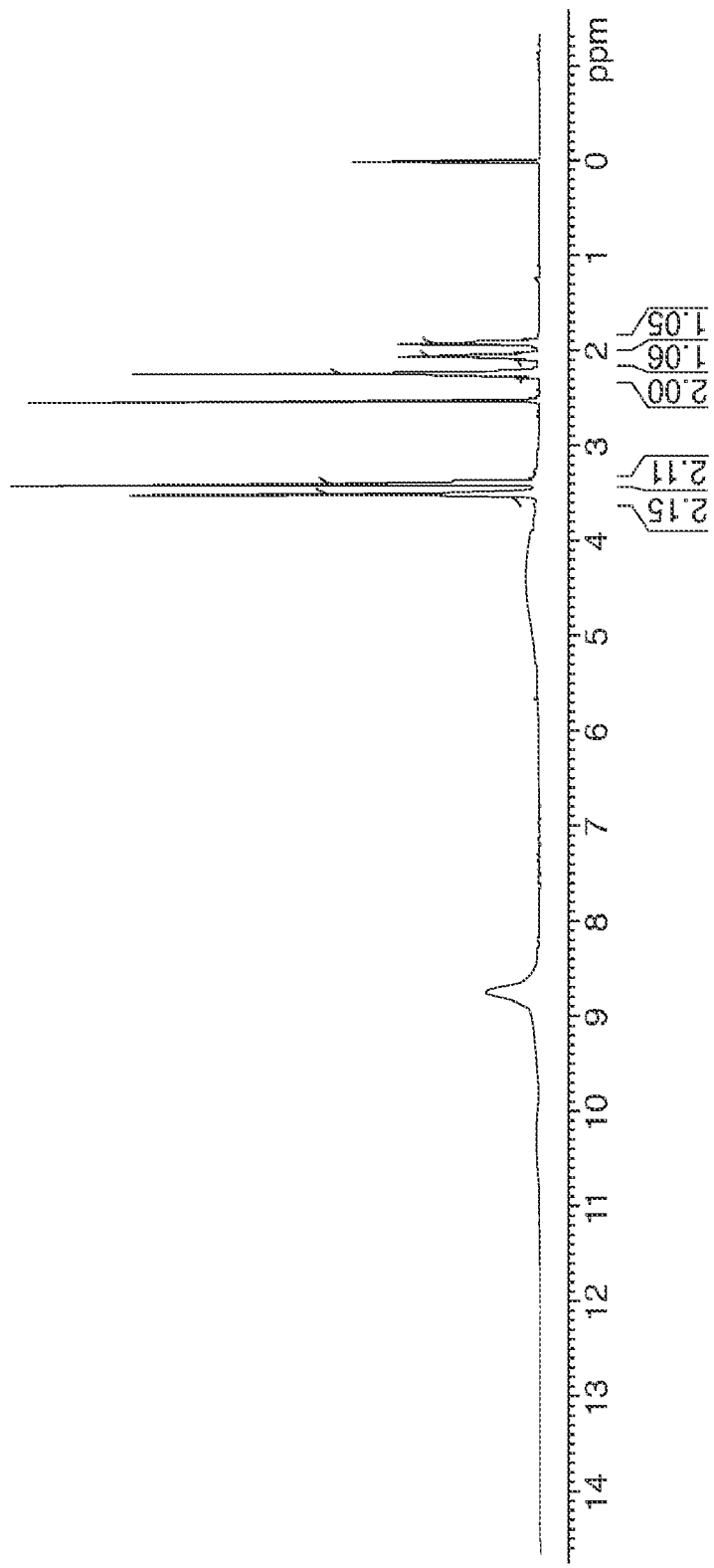
FIG. 12 depicts a $^1$H NMR spectra of a compound disclosed herein.

Chemical shifts are observed as follows: $^1$H, DMSO-d$_6$, 600 MHz, δ in ppm, TMS at 0.00 ppm: 8.72 (bs, 1H), 3.47dd, 2H), 3.37 (t, 2H), 2.21 (m, 2H), 2.02 (m, 1H), 1.89 (m, 1H) (see FIG. 12);

$^{13}$C, DMSO-d$_6$, 150 MHz, δ in ppm, reference DMSO at 39.5 ppm: 169.6, 68.7, 45.6, 40.7, 32.9, 22.4.

The chemical shift of the amide proton was located at 8.72 ppm as a broad singlet, and cross peaks were observed between 8.72 and 3.37. This finding established the chemical shift of H-3 at 3.47 ppm. Weak nOe between 3.37 and 2.21 ppm indicates the populations of H-5 at 2.21 ppm. Total correlation was found from 3.37 to 2.21 ppm through 2.02 1nd 1.89 ppm; nOe correlation was observed between 2.21, 2.02, 1.89 and 3.37 ppm. This finding was understandable as the resonances H-6 and H-7 are: H-6 (2.02 and 1.89 ppm), H-7 (3.37 ppm). The heteronuclear 2-D experiments (HSQC and HMBC) also confirmed the chemical shifts of protons and carbon.

The chemical shift of individual protons and carbon were observed as follows:

8.72 (bs, H-2, 1H), 3.47 (dd, H-3, 2H), 3.37 (t, H-7, 2H), 2.21 (m, H-5, 2H), 2.02 (m, H-6, 1H), 1.89 (m, H-6'1H)

169.6 (C-1), 68.7 (C-4), 45.6 (C-7), 40.7 (C-3), 32.9 (C-5), 22.4 (C-6)

A weak nOe between H-3 and H-5 is suggestive of restricted rotation of the rings with respect to each other. The absence of hydrogen bonds in which the donor and acceptor residues i (i±3) and also absence of long range nOe (C$^\alpha$ atoms<7A°) between two rings indicates there is no significant secondary fold.

Example 11

Proton 1-D experiments $^1$H, $^{13}$C, DEPT, homo nuclear 2-D experiments (DQF-COSY, TOCSY, NOESY) and Hetero nuclear experiments HSQC and HMBC in DMSO-D$_6$ at 30 degree Celsius are conducted to confirm the exact carbon chemical shifts and protons chemical shifts of the spiro compound

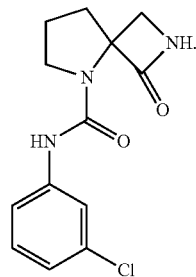 [SMILES: O=C(Nc1cccc(Cl)c1)N1CCCC12CNC2=O]

The $^1$H NMR in DMSO is shown in FIG. 13. A N15-HSQC experiment at 600 MHz can be performed to confirm amide chemical shifts.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference, including the following incorporated by reference:

Abbott F V, Franklin K B, Westbrook R F, The formalin test: scoring properties of the first and second phases of the pain response in rats. Pain, 60 (1995) 91-102; Bennett G J, Xie Y K., A peripheral mononeuropathy in rat that produces disorders of pain sensation like those seen in man. Pain, 33 (1988) 87-107; U.S. Pat. No. 7,273,889; U.S. Pat. No. 6,821, 985; U.S. Pat. No. 6,667,317; U.S. Pat. No. 6,635,270; U.S. Pat. No. 6,521,414; U.S. Pat. No. 6,197,820; U.S. Pat. No. 6,147,230; U.S. Pat. No. 6,007,841; U.S. Pat. No. 5,952,389; U.S. Pat. No. 5,902,815; U.S. Pat. No. 5,741,778; U.S. Pat. No. 5,605,911; U.S. Pat. No. 5,523,323; U.S. Pat. No. 4,959, 493; Moskal, et al. (2005), Neuropharmacology, 49(7):1077-87; Narahshi, Toshio et al. (2004) Biol. Pharm. Bull., 27(1): 1701-1706; Lynch, Gary et al. (2006), Aging Research Reviews, 5:255-280; Rajashankar et al. J. Am. Chem. Soc. (1992), 114, 9225; Rajashankar et al. J. Am. Chem. Soc. (1995), 117, 10129; A. Karle et al, Biochemistry (1990), 29, 6747; Regan et al, Science (1998), 241, 976; Kaumaya et al, Biochemistry (1990), 29, 13; Hanessian et al, Tetrahedron (1997), 53, 12789; Zhang et al, Org. Lett. (2003), 53115; Xuyuan et al, Org. Lett. (2004), 6, 3285; Halab et al, J. Med. Chem. (2002), 45, 5353

---

What is claimed is:

1. A compound represented by:

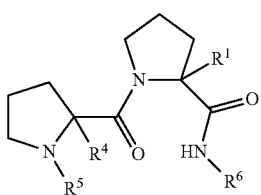

wherein
$R^4$ is H;
$R^1$ is benzyl;
$R^5$ is

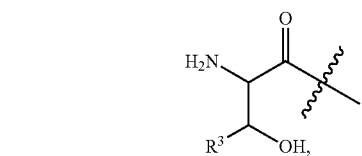

$R^6$ is

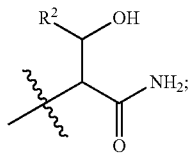

$R^2$ is H or $CH_3$,
$R^3$ is H or $CH_3$, and stereoisomers, N-oxides or pharmaceutically acceptable salts thereof.

2. A pharmaceutically acceptable composition comprising a compound of claim 1, and a pharmaceutically acceptable excipient.

3. The compound of claim 1, wherein $R^2$ and $R^3$ are $CH_3$.

4. The compound of claim 1, wherein $R^2$ is $CH_3$ and $R^3$ is H.

5. The compound of claim 1, represented by:

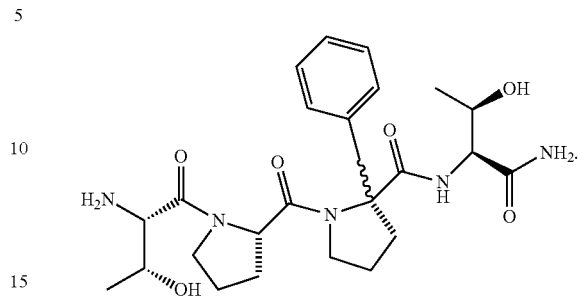

6. A compound represented by:

(SEQ ID NO: 2)

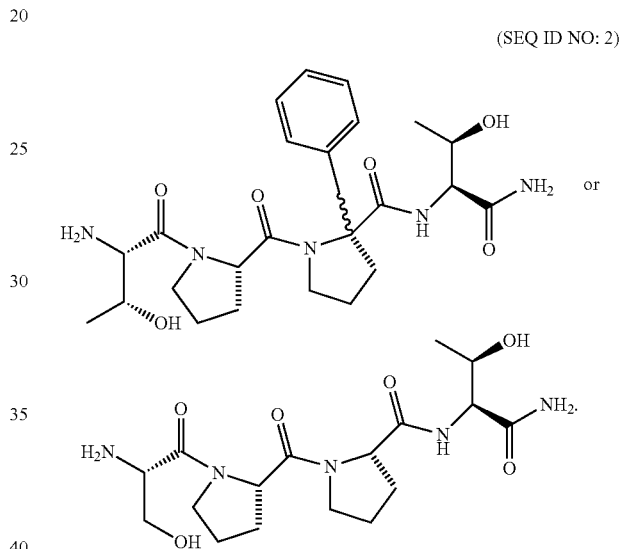

* * * * *

SEQUENCE LISTING

<160> NUMBER OF SEQ ID NOS: 5

<210> SEQ ID NO 1
<211> LENGTH: 292
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Gly Met Ser Thr Arg Leu Lys Ile Val Thr Ile His Gln Glu Pro Phe
1               5                   10                  15

Val Tyr Val Lys Pro Thr Met Ser Asp Gly Thr Cys Lys Glu Glu Phe
            20                  25                  30

Thr Val Asn Gly Asp Pro Val Lys Lys Val Ile Cys Thr Gly Pro Asn
        35                  40                  45

Asp Thr Ser Pro Gly Ser Pro Arg His Thr Val Pro Gln Cys Cys Tyr
    50                  55                  60

Gly Phe Cys Ile Asp Leu Leu Ile Lys Leu Ala Arg Thr Met Asn Phe
65                  70                  75                  80

Thr Tyr Glu Val His Leu Val Ala Asp Gly Lys Phe Gly Thr Gln Glu
                85                  90                  95

Arg Val Asn Asn Ser Asn Lys Lys Glu Trp Asn Gly Met Met Gly Glu
            100                 105                 110

Leu Leu Ser Gly Gln Ala Asp Met Ile Val Ala Pro Leu Thr Ile Asn
        115                 120                 125

Asn Glu Arg Ala Gln Tyr Ile Glu Phe Ser Lys Pro Phe Lys Tyr Gln
    130                 135                 140

Gly Leu Thr Ile Leu Val Lys Lys Gly Thr Arg Ile Thr Gly Ile Asn
145                 150                 155                 160

Asp Pro Arg Leu Arg Asn Pro Ser Asp Lys Phe Ile Tyr Ala Thr Val
                165                 170                 175

Lys Gln Ser Ser Val Asp Ile Tyr Phe Arg Arg Gln Val Glu Leu Ser
            180                 185                 190

Thr Met Tyr Arg His Met Glu Lys His Asn Tyr Glu Ser Ala Ala Glu
        195                 200                 205

Ala Ile Gln Ala Val Arg Asp Asn Lys Leu His Ala Phe Ile Trp Asp
    210                 215                 220

Ser Ala Val Leu Glu Phe Glu Ala Ser Gln Lys Cys Asp Leu Val Thr
225                 230                 235                 240

Thr Gly Glu Leu Phe Phe Arg Ser Gly Phe Gly Ile Gly Met Arg Lys
                245                 250                 255

Asp Ser Pro Trp Lys Gln Asn Val Ser Leu Ser Ile Leu Lys Ser His
            260                 265                 270

Glu Asn Gly Phe Met Glu Asp Leu Asp Lys Thr Trp Val Arg Tyr Gln
        275                 280                 285

Glu Cys Asp Ser
    290

<210> SEQ ID NO 2
<211> LENGTH: 4

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 2

Ser Pro Pro Thr
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 3

Thr Pro Pro Ser
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 4

Ser Pro Pro Ser
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term amidated

<400> SEQUENCE: 5

Thr Pro Pro Thr
1
```